(12) United States Patent
Donde et al.

(10) Patent No.: US 7,732,443 B2
(45) Date of Patent: Jun. 8, 2010

(54) THERAPEUTIC SUBSTITUTED CYCLOPENTANES

(76) Inventors: Yariv Donde, 24386 Antilles Way, Dana Point, CA (US) 92629; Robert M. Burk, 1337 Cerritos Dr., Laguna Beach, CA (US) 92651; Jeremiah H. Nguyen, 16146 Bamboo St., La Puente, CA (US) 91744

( * ) Notice: Subject to any disclaimer, the term of this patent is extended or adjusted under 35 U.S.C. 154(b) by 0 days.

(21) Appl. No.: 12/404,753

(22) Filed: Mar. 16, 2009

(65) Prior Publication Data
US 2009/0239869 A1    Sep. 24, 2009

Related U.S. Application Data

(60) Provisional application No. 61/037,625, filed on Mar. 18, 2008.

(51) Int. Cl.
*A61K 31/216* (2006.01)
*A61K 31/5377* (2006.01)
*C07D 265/30* (2006.01)
*C07C 57/26* (2006.01)

(52) U.S. Cl. .................... 514/231.2; 514/555; 544/106; 562/503

(58) Field of Classification Search ................. 544/106; 562/503; 514/231.2, 555
See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 5,462,968 A | 10/1995 | Woodward |
| 5,698,598 A | 12/1997 | Woodward |
| 6,090,847 A | 7/2000 | Woodward |
| 6,437,146 B1 | 8/2002 | Hattori et al. |
| 6,710,072 B2 * | 3/2004 | Burk et al. .................. 514/438 |
| 7,091,231 B2 | 8/2006 | Donde et al. |

OTHER PUBLICATIONS

Chourasia, M.K.; Jain, S.K.: Pharmaceutical Approaches to Colon Targeted Drug Delivery Systems. J Pharm Pharmaceut Sci 6 (1): 33-66, 2003.
Myers, Andrew; Dragovich, Peter: a Reaction Cascade Leading to 1,6-Didehydro[10]annulene→1,5-Dehydronaphthalene Cyclization Initiated by Thiol Addition. J. Am. Chem. Soc. 1993, 115, 7021.
Reich, S.H. et al.: Substituted Benzamide Inhibitors of Human Rhinovirus 3C Protease: Structure-Based Design, Synthesis, and Biological Evaluation. J. Med. Chem. 2000, 43, p. 1670.
Remington's Pharmaceutical Sciences, Mack Publishing Company, Easton, Pa., 16th Edition, 1980.
Shareef, Ajmal; et al.: Colonic Drug Delivery: An Updated Review. AAPS PharmSci 2003; 5(2) Article 17.

* cited by examiner

*Primary Examiner*—Kamal A Saeed
*Assistant Examiner*—Janet L Coppins
(74) *Attorney, Agent, or Firm*—Monique M. Butler

(57) ABSTRACT

Therapeutic compounds are disclosed herein. Methods, compositions, and medicaments related thereto are also disclosed. The compounds described herein are used to treat ocular conditions, bowel disease and baldness.

6 Claims, No Drawings

THERAPEUTIC SUBSTITUTED CYCLOPENTANES

RELATED APPLICATION

This application claims priority to U.S. Provisional Patent Application Ser. No. 61/037,625 filed on Mar. 18, 2008 and which is incorporated herein in its entirety by this specific reference.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

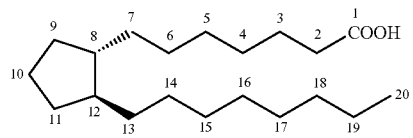

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

The prostaglandin E analog shown below is disclosed in the following documents, expressly incorporated herein by reference: U.S. Pat. No. 5,462,968; U.S. Pat. No. 5,698,598; and U.S. Pat. No. 6,090,847.

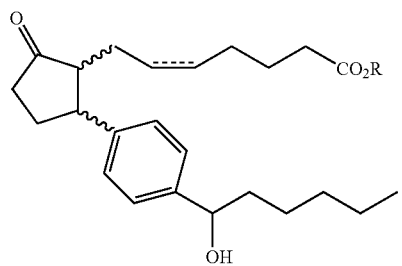

Prostaglandin $EP_2$ selective agonists are useful for treating glaucoma, and are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., apthhous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP$_2$ agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

A compound comprising

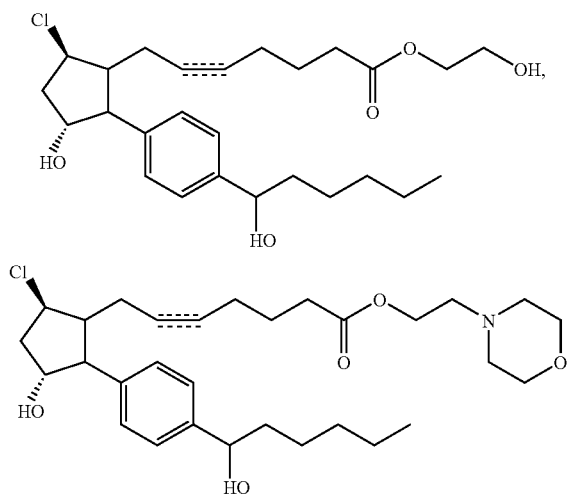

or a pharmaceutically acceptable salt or prodrug thereof, wherein a dashed line indicates the presence or absence of a bond, is disclosed herein.

As a dashed line indicates the presence or absence of a bond, the compounds shown below, or pharmaceutically acceptable salts or prodrugs thereof, are possible.

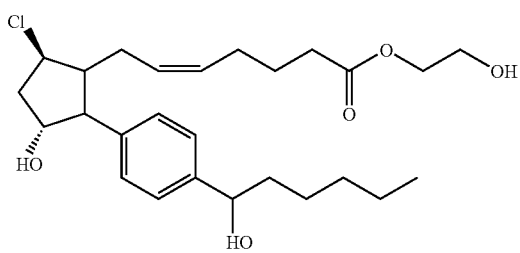

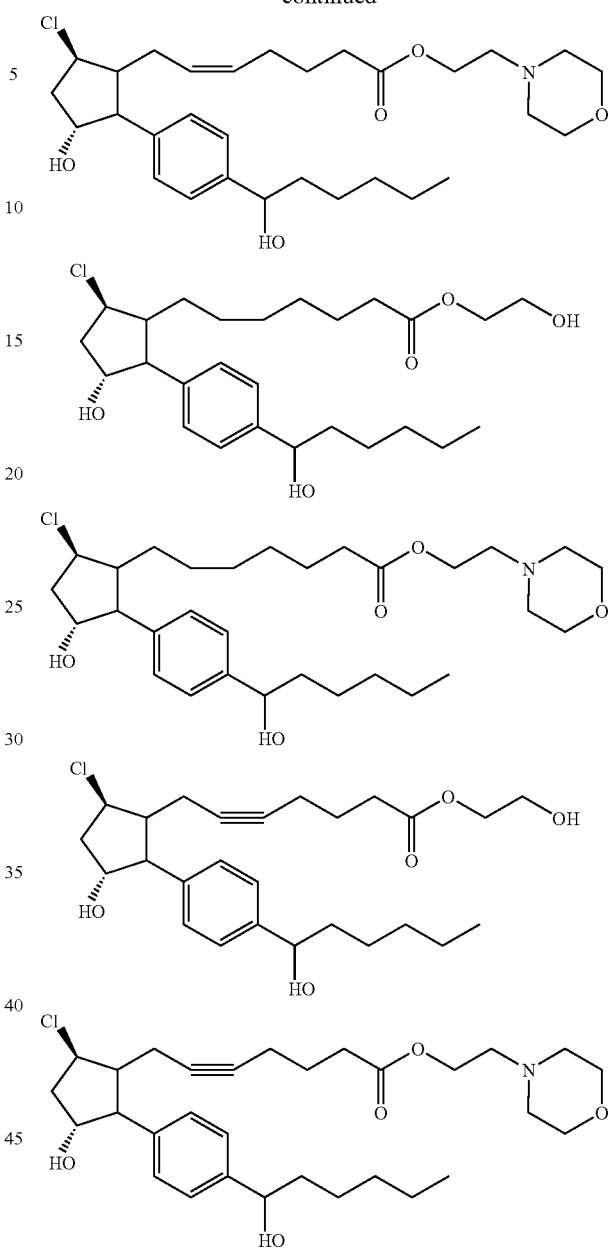

While not intending to limit the scope of the invention in any way, compounds having the stereochemistry indicated in the structures below, and pharmaceutically acceptable salts and prodrugs thereof, are specifically contemplated.

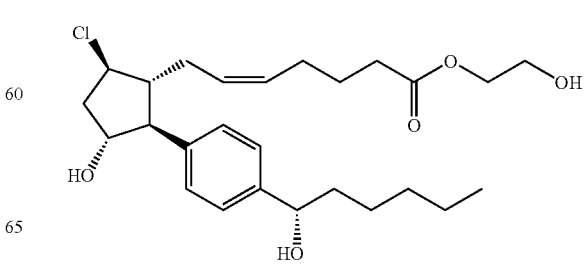

-continued
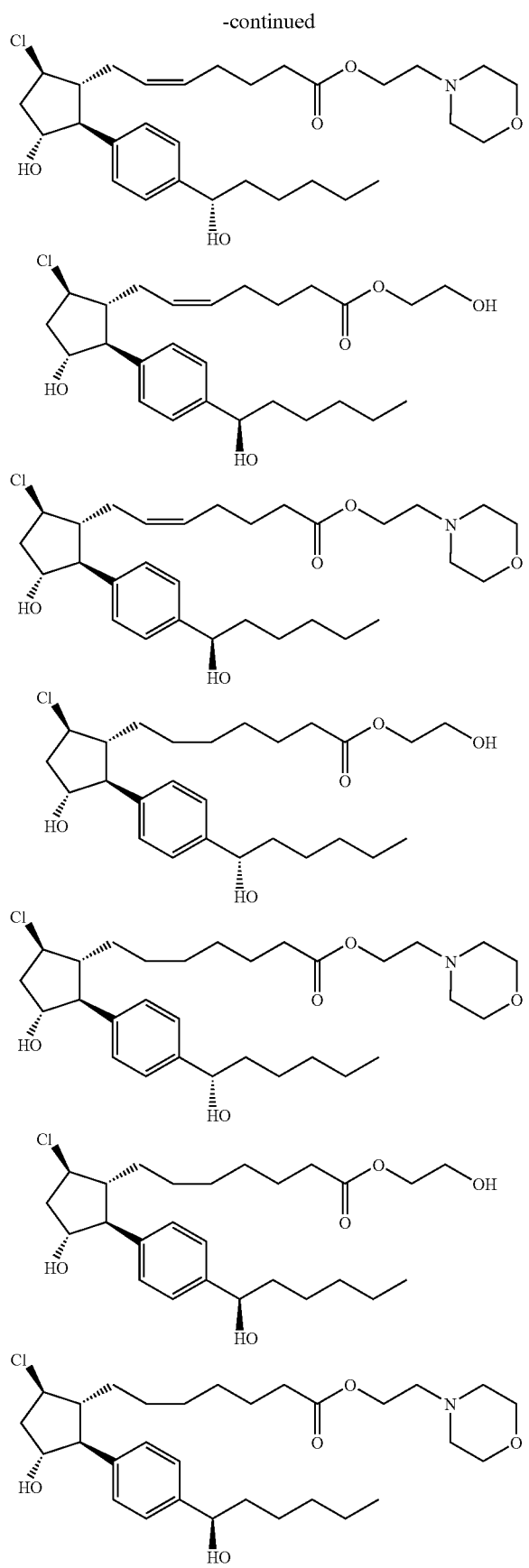
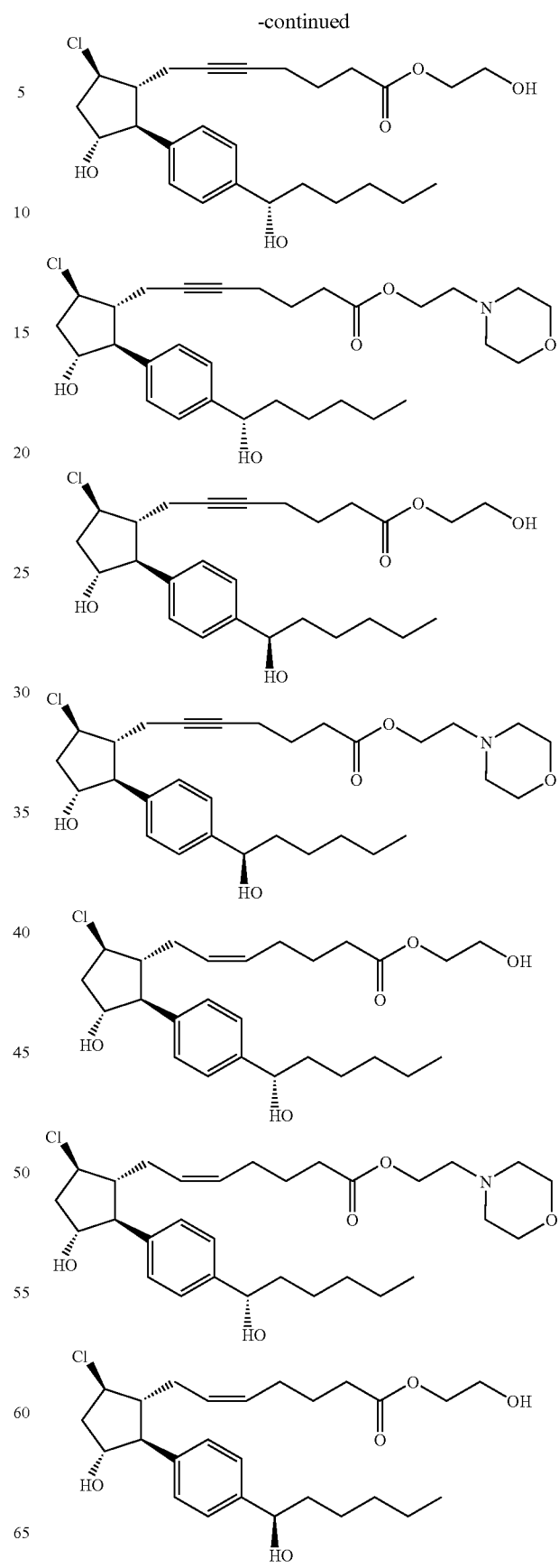

-continued

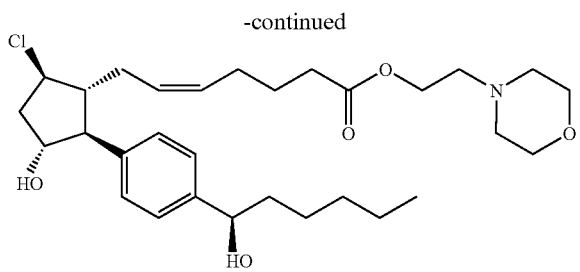

The compounds of disclosed herein are useful for the prevention or treatment of glaucoma or ocular hypertension in mammals, or for the manufacture of a medicament for the treatment of glaucoma or ocular hypertension. Additionally, the compounds described herein can be useful in treating baldness. They are also useful for the treatment of those diseases disclosed in the art as being amenable to treatment by prostaglandin $EP_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1-6 carbon atoms, etc. A $C_{1-6}$ alkyl ester has an alkyl moiety of from 1 to 6 carbons directly attached to the oxygen of the ester.

The following compounds are also contemplated, as well as any pharmaceutically acceptable salt, or any prodrug thereof, are specifically contemplated herein. All compounds are mixtures of diastereomers except where indicated:

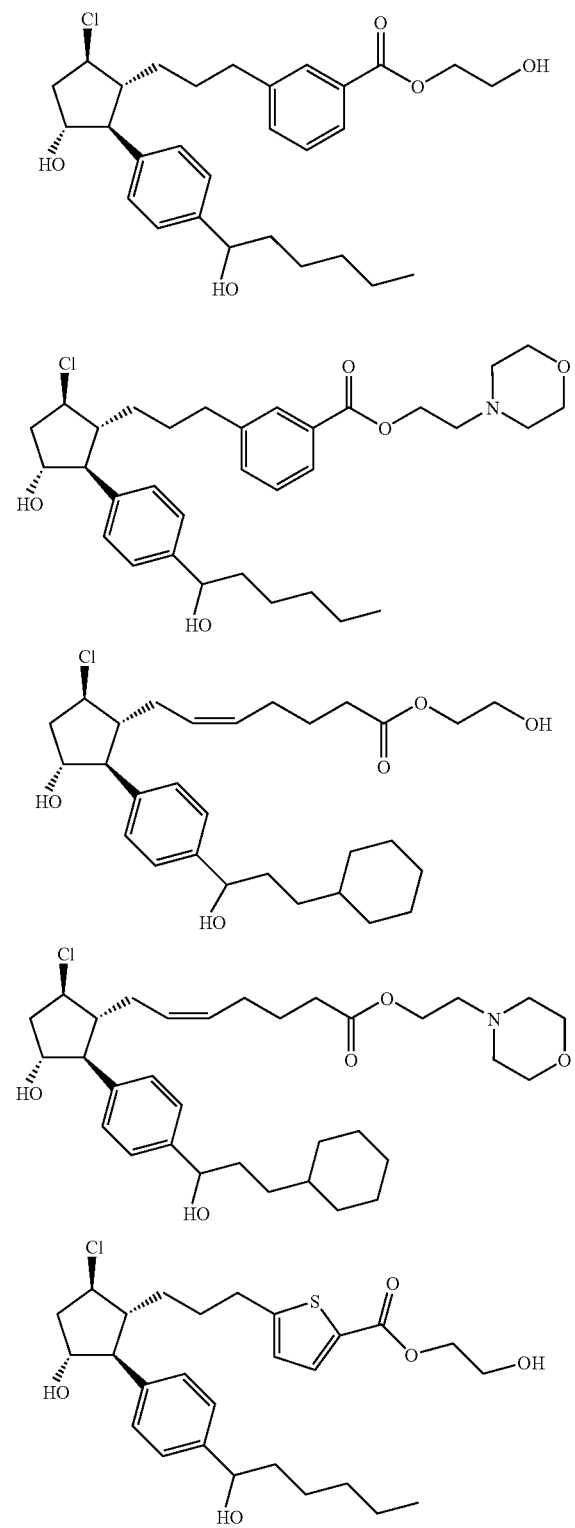

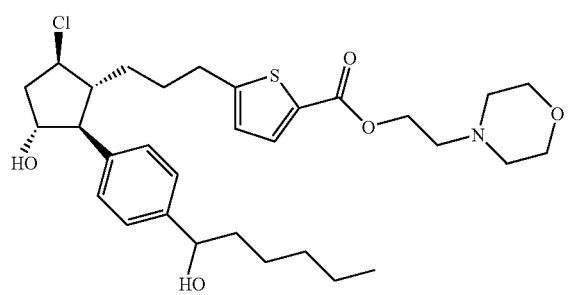
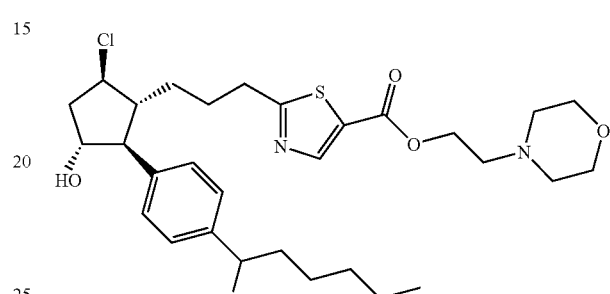
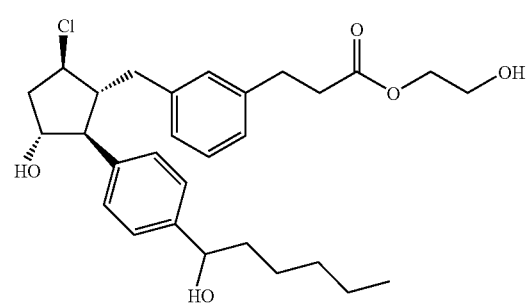
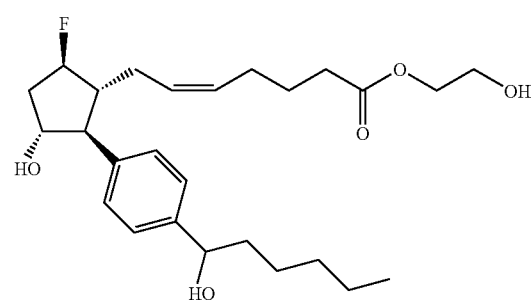
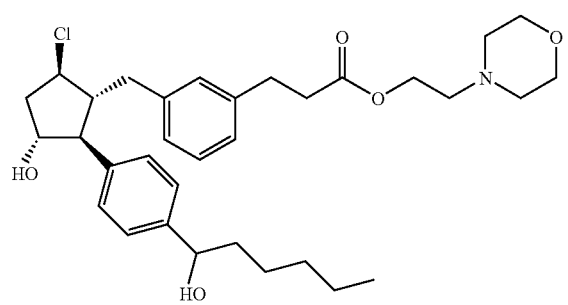
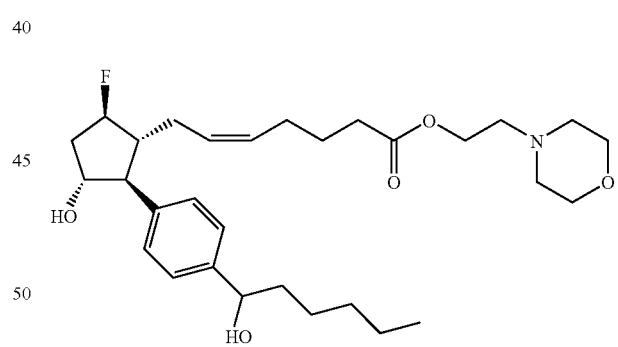
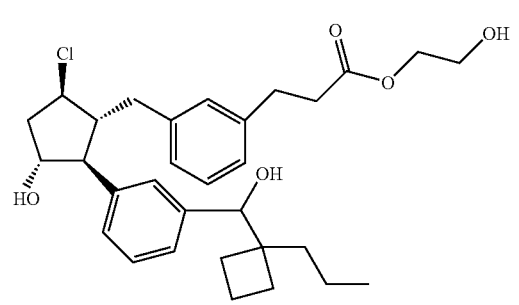
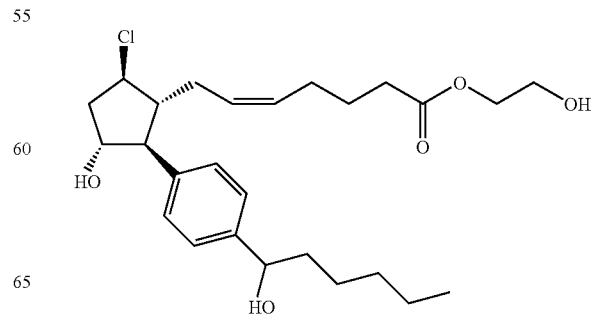
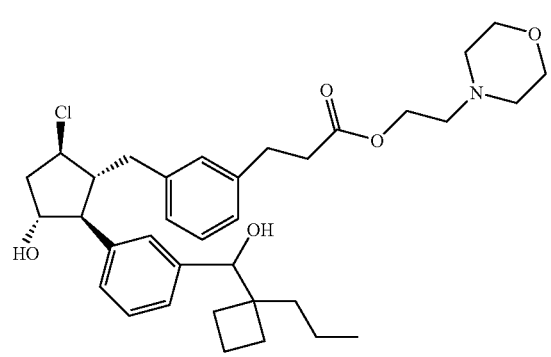

-continued
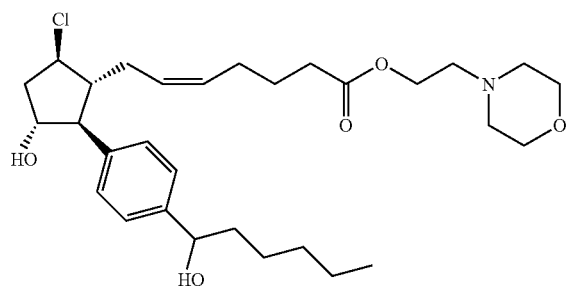
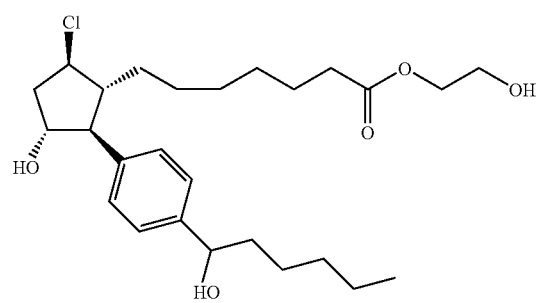
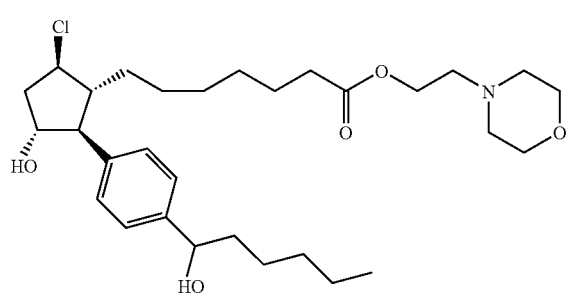
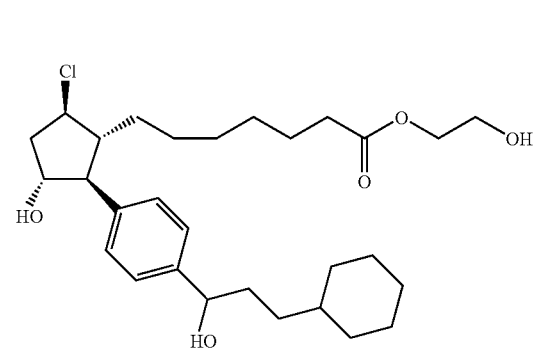
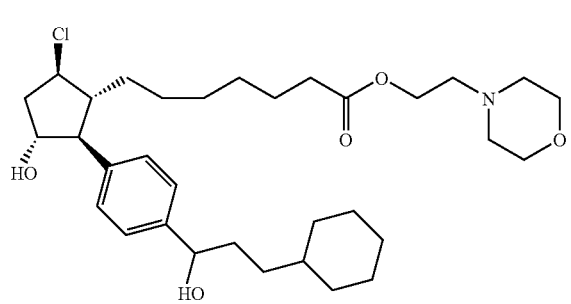
-continued
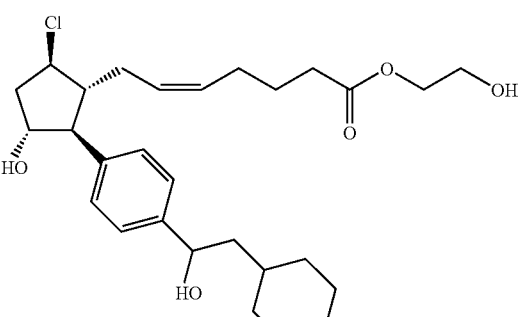
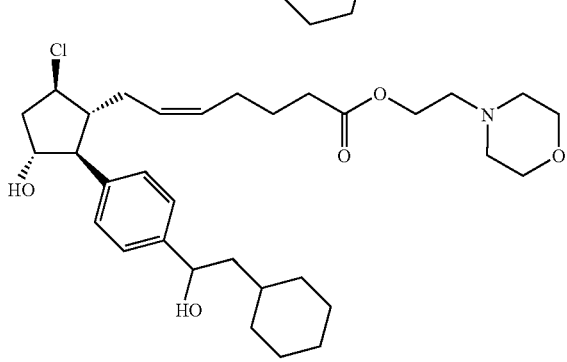
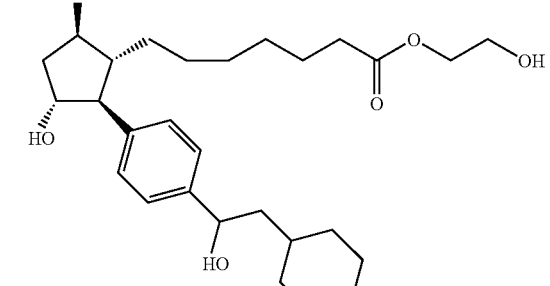
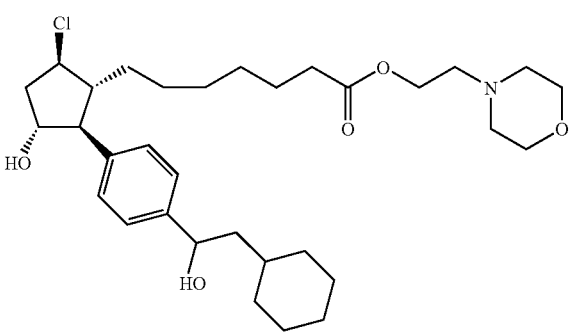
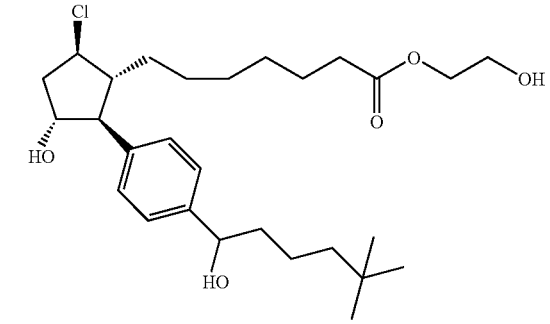

13
-continued
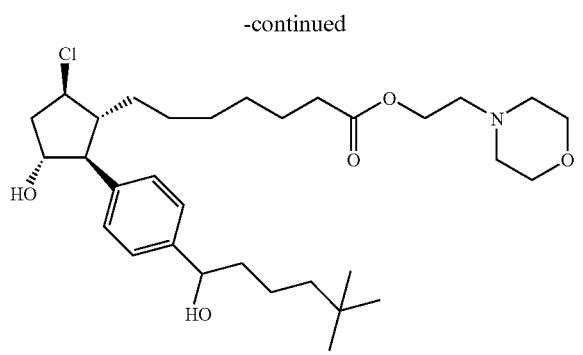
14
-continued
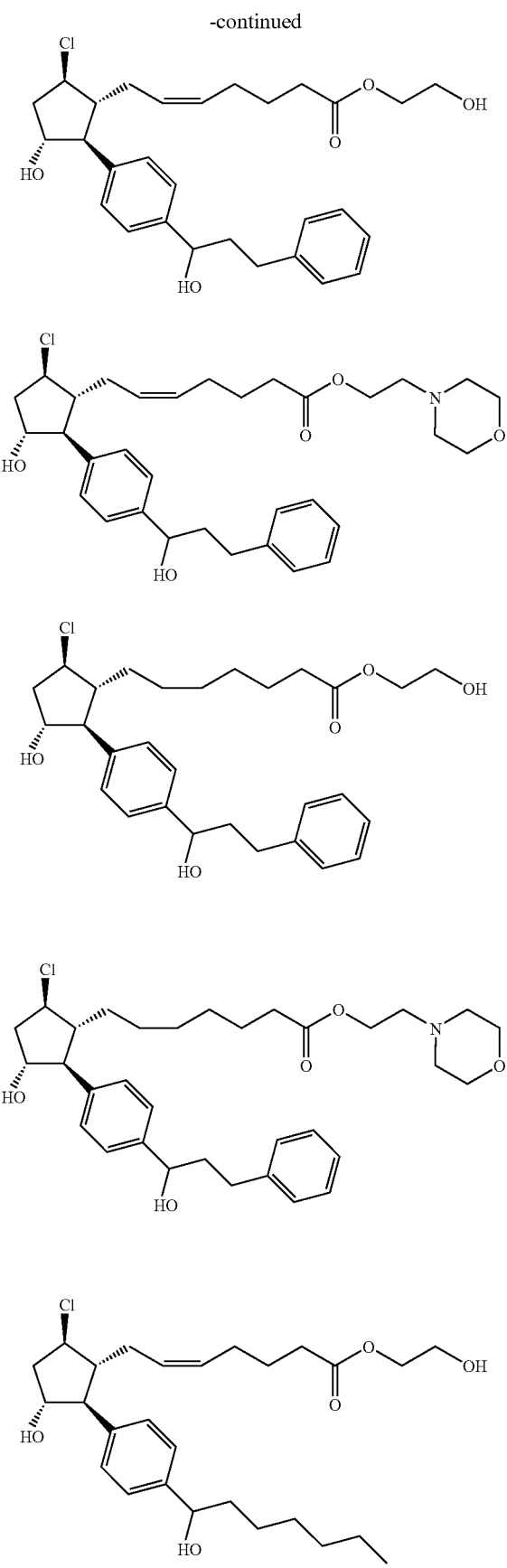

-continued
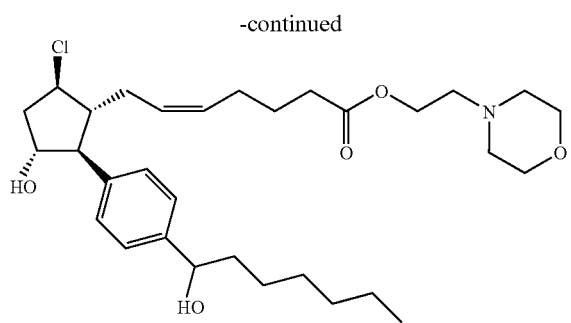
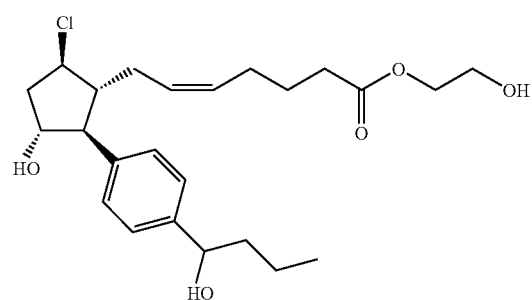
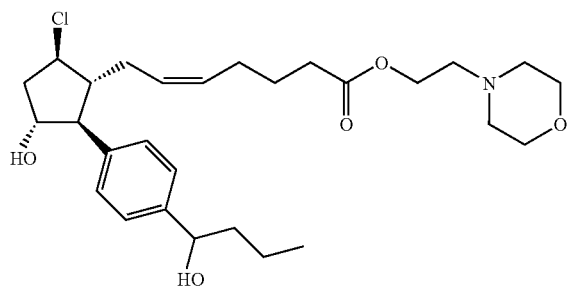
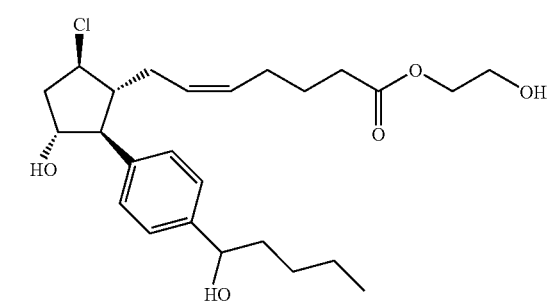
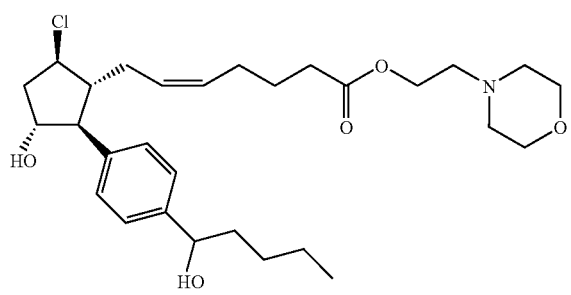
-continued
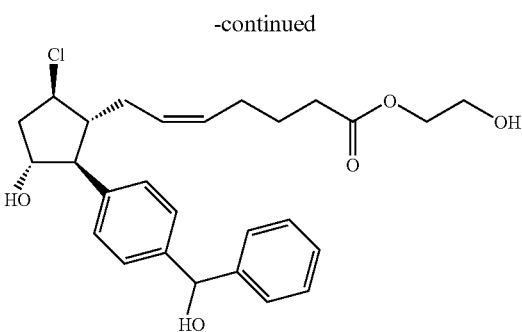
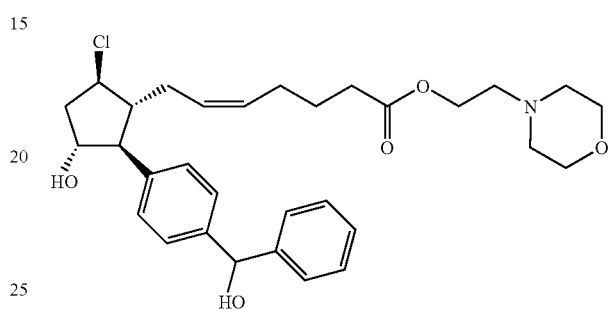
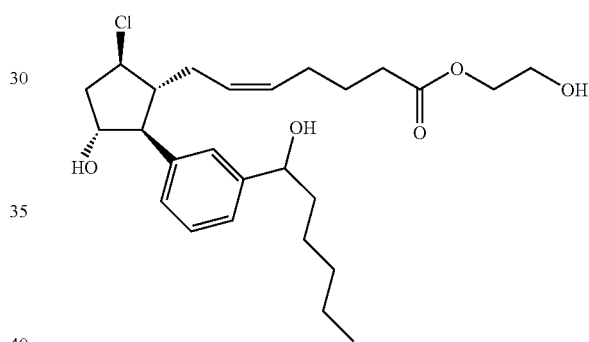
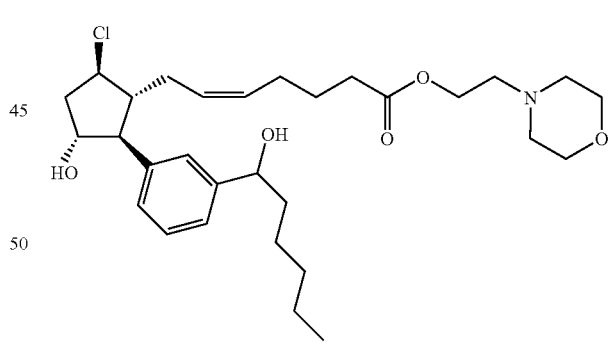
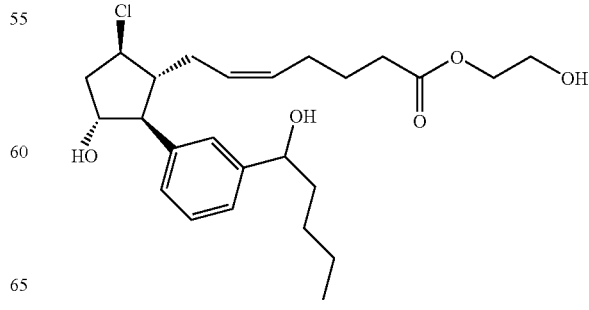

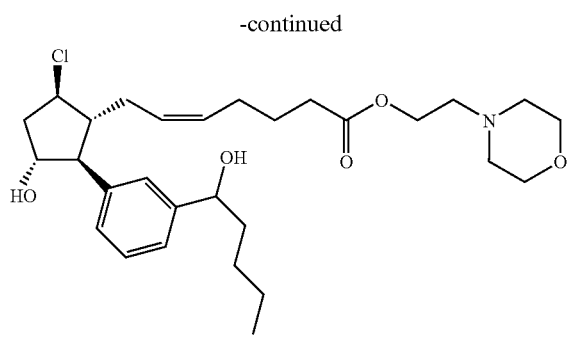
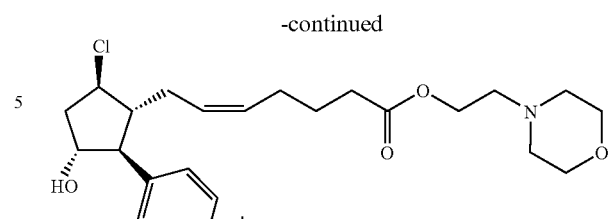
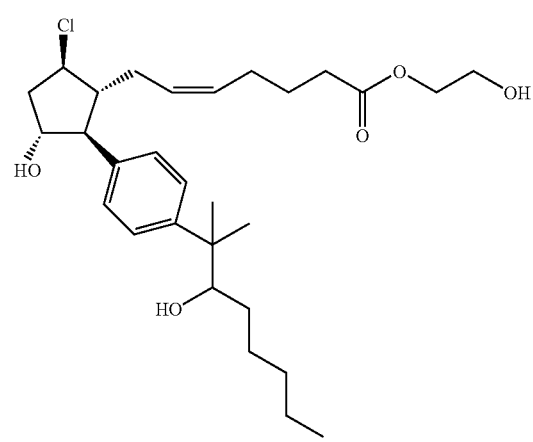
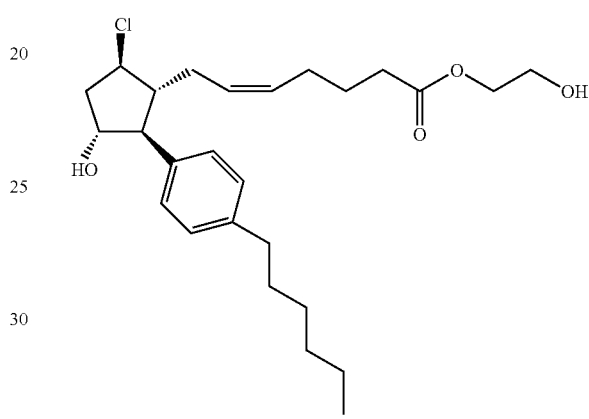
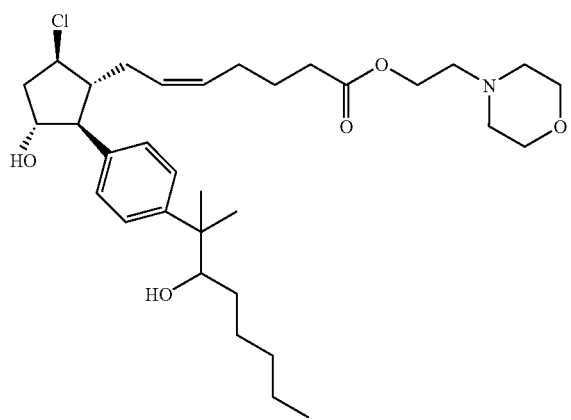
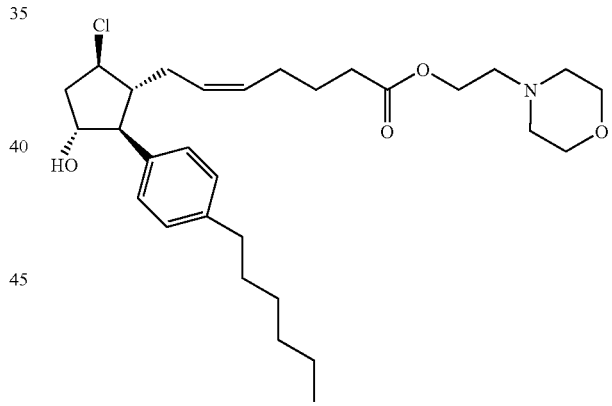
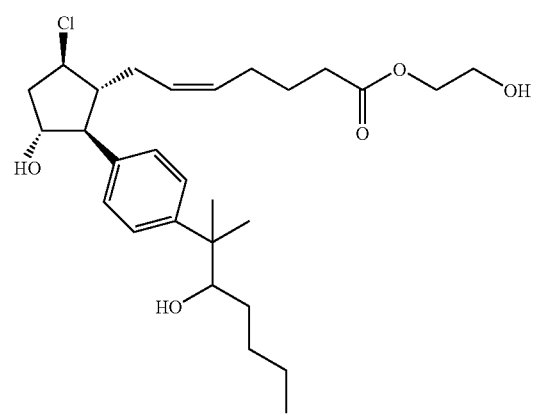
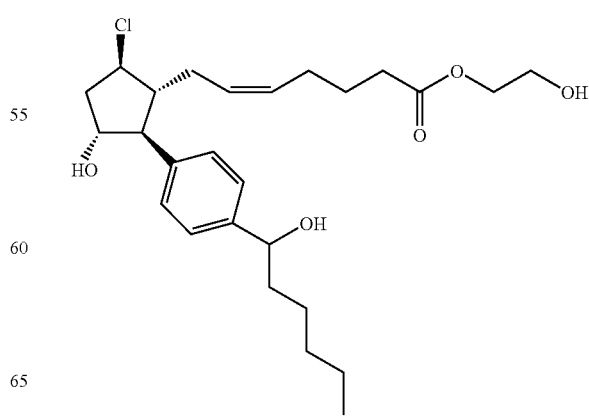

-continued

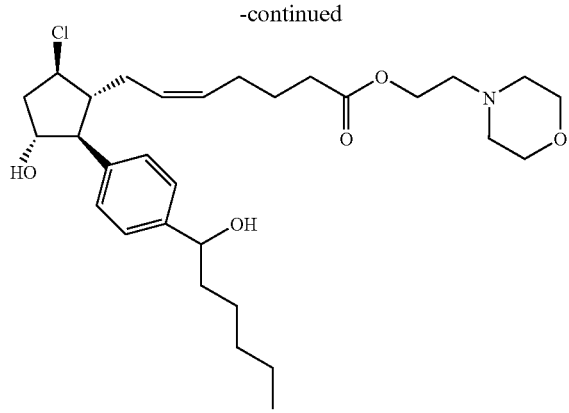

One embodiment is use of any compound disclosed herein, including those disclosed above, in the manufacture of a medicament for the treatment of glaucoma or ocular hypertension.

Another embodiment is use of any compound disclosed herein, including those disclosed above, in the manufacture of a medicament for the treatment of an inflammatory bowel disease.

Another embodiment is a method comprising administering any compound disclosed herein, including those disclosed above, topically to an eye of a mammal for the treatment of glaucoma or ocular hypertension.

Another embodiment is use of any compound disclosed herein, including those disclosed above, in the manufacture of a medicament for the treatment of baldness.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chlorostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

These compounds can also be used to treat or prevent conditions affecting the posterior part of the eye include maculopathies/retinal degeneration such as non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitus, or cytomegalovirus retinitis.

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiogicla acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

These compounds are also useful in treating asthma.

EXAMPLES

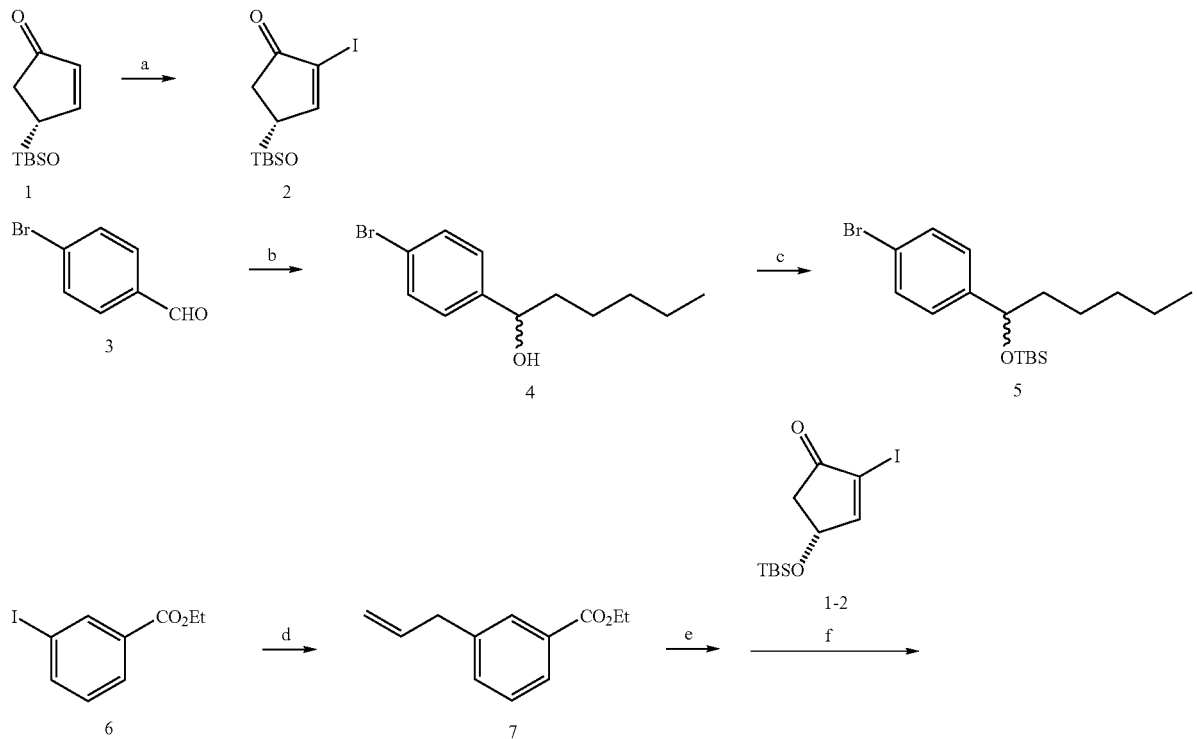

Scheme 1

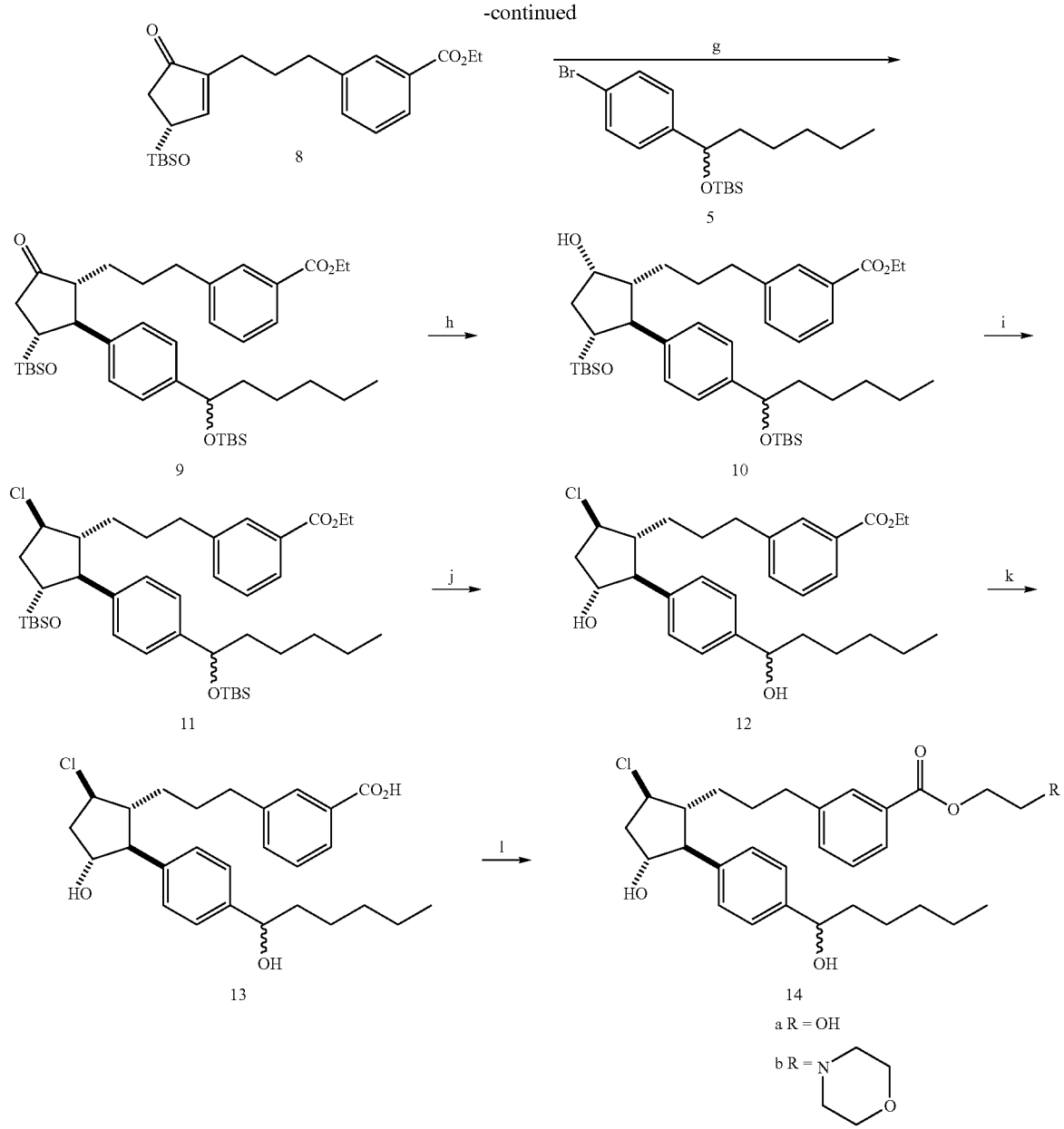

(a) I₂, pyridine, CH₂Cl₂; (b) n-pentylMgBr; (c) TBSOTf, 2,6-lutidine, CH₂Cl₂; (d) i-PrMgCl; cat. CuCN, allylbromide; (e) 9-BBN; (f) PdCl₂(dppf), K₃PO₄, DMF; (g) t-BuLi; 2-ThienylCuCNLi; (h) L-selectride; (i) MsCl, TEA; TBAC 40° C. (j) HF•pyridine 0° C.; (k) 1M LiOH, THF; (l) 1. ClCO₂Et, Et₃N, CH₂Cl₂, 2. RCH₂CH₂OH.

(R)-4-tert-Butyl-dimethyl-silanyloxy)-2-iodo-cyclopent-2-enone (2). A procedure similar to the one described in A. G. Myers and P. S. Dragovich *J. Am. Chem. Soc.* 1993,115,7021 was followed. A 0° C. solution of enone 1 (3.163 g, 14.9 mmol, Evotec OAI, 151 Milton Park, Abington, Oxon, OX 14 4SD, UK) and pyridine (5 mL) in dichloromethane (5 mL) was treated with a solution of I₂ (6.511 g, 25.7 mmol) in pyridine (12 mL)/dichloromethane (12 mL). The reaction was allowed to warm to room temperature and after 2 h, 1M HCl (60 mL) was added. The resulting mixture was poured into 100 mL 1M HCl and then was extracted with dichloromethane (3×60 mL). The combined dichloromethane solution was washed with saturated NaHSO₃ solution and with brine and then was dried (Na₂SO₄), filtered and evaporated. Purification by flash chromatography on silica gel (5% ethyl acetate/hexanes) gave compound 2 (4.600 g, 91%).

1-(4-Bromo-phenyl)-hexan-1-ol (4). n-PentylMgBr (29 mL, 58 mmol, 2 M/ether) was added to a 0° C. solution of 4-bromobenzaldehyde (9.953 g, 54 mmol) in THF (100 mL). After 1 h, the reaction was quenched by addition of 200 mL saturated ammonium chloride solution. The resulting mixture was extracted with ethyl acetate (3×100 mL) and the combined ethyl acetate solution was dried (Na2SO4), filtered and evaporated. Purification of the residue by flash chromatography on silica gel gave 4 (10.501 g, 76%).

[1-(4-Bromo-phenyl)-hexyloxy]-tert-butyl-dimethyl-silane (5). TBSOTf (2.9 mL, 12.6 mmol) was added to an ice-cold solution of 4 (3.017 g, 11.7 mmol) and 2,6-lutidine (1.6 mL, 13.7 mmol) in dichloromethane (30 mL). The reaction was stirred for 2 h at room temperature and then 100 mL saturated sodium bicarbonate solution was added. The resulting mixture was extracted with dichloromethane (30 mL) and the dichloromethane layer was washed with 1 M HCl (2×50 mL) and brine (50 mL). The dichloromethane solution was then dried ($MgSO_4$), filtered and evaporated. Purification of the residue by flash chromatography on silica gel (hexanes) gave compound 5 (3.843 g, 88%).

3-Allyl-benzoic acid ethyl ester (7). A −45° C. solution of ethyl 3-iodobenzoate (2.434 g, 8.8 mmol) in 40 mL THF was treated with i-PrMgCl (4.8 mL, 9.6 mmol, 2 M/ether). After 1 h, allyl bromide (1.6 mL, 18.9 mmol) was added followed by CuCN (79 mg, 0.88 mmol). The reaction was stirred for 1 h and then was quenched by addition of 50 mL saturated $NH_4Cl$ solution. Water (30 mL) was added and the resulting mixture was extracted with ethyl acetate (3×50 mL). The combined ethyl acetate solution was dried ($MgSO_4$), filtered and evaporated. Purification by flash chromatography on silica gel (5% ethyl acetate/hexanes→10%) gave compound 7 (1.145 g, 68%).

3-{3-[(R)-3-tert-Butyl-dimethyl-silanyloxy)-5-oxo-cyclopent-1-enyl]-propyl}-benzoic acid ethyl ester (8). A solution of 7 (303 mg, 1.6 mmol) in 0.5 mL THF was added to a solution of 9-BBN dimer (393 mg, 1.6 mmol) in 6 mL THF. After 4 h, 0.1 mL $H_2O$ was added. The solution was stirred for 20 min. and then was cannula transferred to a mixture of $PdCl_2$(dppf) (78 mg, 0.11 mmol) and 2 (387 mg, 2.0 mmol) in DMF (3.2 mL). $K_3PO_4$ (0.7 mL, 2.1 mmol, 3 M) was added and the dark solution was stirred for 1.25 h. The solution was then poured into 50 mL brine and the resulting mixture was extracted with ethyl acetate (2×30 mL). The combined ethyl acetate solution was dried ($MgSO_4$), filtered and evaporated. Purification by flash chromatography on silica gel gave 292 mg (46%) of enone 8.

1-8→→3-(3-{(1R,2S,3R,5R)-5-Chloro-3-hydroxy-2-[4-(1-hydroxy-hexyl)-phenyl]-cyclopentyl}-propyl)-benzoic acid (13). The sequence leading to 13 was completed as shown in scheme 1 and as described in U.S. patent application Ser. No. 11/009,298, filed on Dec. 10, 2004 (now U.S. Pat. No. 7,091,231 issued Aug. 15, 2006), expressly incorporated by reference herein, FIGS. 5,6.

Compound 14a. Triethylamine and ethyl chloroformate are added sequentially to a solution of compound 13 in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1N HCl then dried ($MgSO_4$), filtered and concentrated in vacuo. Purification of the residue by flash column chromatography on silica gel (10% $CH_3OH/CH_2Cl_2$) affords compound 14a.

Compound 14b. Triethylamine and ethyl chloroformate are added sequentially to a solution of compound 13 in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 14b.

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid methyl ester. The title compound was prepared using an analogous procedure to that described for 1-12, starting with 5-Bromo-thiophene-2-carboxylic acid methyl ester, which was prepared from 5-Bromo-thiophene-2-carboxylic acid as follows: Acetyl chloride (6.87 mL, 96.6 mmol) was added to a solution of 5-Bromo-thiophene-2-carboxylic acid (4.0 g, 19.3 mmol) in methanol (30 mL). The reaction was allowed to stir overnight and then was heated to reflux for 1.5 h. The reaction was allowed to cool to room temperature and then was evaporated. The residue was treated with 120 mL saturated sodium bicarbonate solution and the resulting mixture was extracted with dichloromethane (3×100 mL). The combined dichloromethane solution was dried ($Na_2SO_4$), filtered and evaporated to give 3.57 g (84%) of 5-Bromo-thiophene-2-carboxylic acid methyl ester.

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid. The title compound was prepared by hydrolysis of the methyl ester using the rabbit liver esterase procedure described in U.S. patent application Ser. No. 11/009,298, filed on Dec. 10, 2004 (now U.S. Pat. No. 7,091,231 issued Aug. 15, 2006).

5-(3-{(1R,2S,3R,5R)-5Chloro-3-hydroxy-2-[4-(1-hydroxy-hexyl)-phenyl]-cyclopentyl}-propyl)-thiophene-2-carboxylic acid isopropyl ester. The title compound was prepared from the corresponding acid using the standard procedure described in U.S. patent application Ser. No. 11/009,298, filed on Dec. 10, 2004 (now U.S. Pat. No. 7,091,231 issued Aug. 15, 2006).

Scheme 2

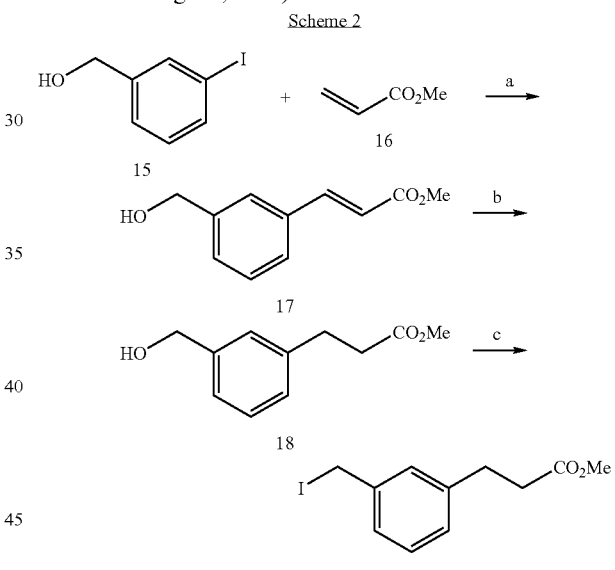

(a) Pd(OAc)$_2$, Et$_3$N CH$_3$CN 100° C.; (b) H$_2$, (Ph$_3$P)$_3$RhCl, EtOH; (c) Ph$_3$P, I$_2$, imidazole, ClCH$_2$CH$_2$Cl.

(E)-3-(3-Hydroxymethyl-phenyl)-acrylic acid methyl ester (17). The procedure described in Reich, S. H. etal. *J. Med. Chem.* 2000, 43, 1670 was followed. Pd(OAc)$_2$ (8.2 mg, 0.037 mmol) and triethylamine (0.360 mL, 2.58 mmol) were added to a solution of 3-iodobenzyl alcohol 15 (0.27 mL, 2.13 mmol) and methyl acrylate 16 (0.220 mL, 2.44 mmol) in CH$_3$CN (4.5 mL). The reaction vessel was sealed with a Teflon screw-cap and was heated at 100° C. for 5 h. At this time, the reaction was allowed to cool to room temperature and the tube was charged with 0.22 mL more of methyl acrylate, 11.7 mg Pd(OAc)$_2$ and 0.360 mL triethylamine. The reaction was heated at 100° C. overnight and then 10 mL saturated ammonium chloride solution was added. The resulting mixture was extracted with dichloromethane (3×40 mL) and the combined dichloromethane solution was dried (Na$_2$SO$_4$), filtered and evaporated. Purification by flash chromatography on silica gel (30% ethyl acetate/hexanes) gave 395 mg (97%) of compound 17.

3-(3-Hydroxymethyl-phenyl)-propionic acid methyl ester (18). (Ph$_3$P)$_3$RhCl (11.5 mg, 0.012 mmol) was added to a solution of 17 (25 mg, 0.13 mmol) in 0.400 mL ethanol. The reaction was stirred under 1 atm H$_2$ balloon for 20 h and then was filtered through Celite. Evaporation to dryness and purification by flash chromatography on silica gel (30% ethyl acetate/hexanes) gave compound 18 (21 mg, 82%).

3-(3-Iodomethyl-phenyl)-propionic acid methyl ester (19). A mixture of Ph$_3$P (36 mg, 0.14 mmol), I$_2$ (41 mg, 0.16 mmol) and imidazole (10.5 mg, 0.15 mmol) in 0.40 mL 1,2-dichloroethane was stirred for 15 min. and then a solution of 18 (20.5 mg, 0.11 mmol) in 0.1 mL 1,2-dichloroethane was added by cannula. The resulting mixture was stirred for 1 h and then was filtered through basic alumina, washing with ethyl acetate. The filtrate was evaporated and the residue was purified by flash chromatography on silica gel to give compound 19 (26 mg, 81%).

3-[3-((1R,2S,3R)-3-(tert-Butyl-dimethyl-silanyloxy)-2-{4-[1-(tert-butyl-dimethyl-silanyloxy)-hexyl]-phenyl}-5-oxo-cyclopentylmethyl)-phenyl]-propionic acid methyl ester (20). A −78° C. solution of aryl bromide 5 (759 mg, 2.0 mmol) in THF (3 mL) was treated with tert-butyllithium (2.6 mL, 4.4 mmol, 1.7 M/pentane). After 30 min., Me$_2$Zn (1.1 mL, 2.2 mmol, 2 M/toluene) was added and the resulting solution was stirred for 15 min. at 0° C. and then was recooled to −78° C. A solution of enone 1 (319 mg, 1.5 mmol, Evotec OAI, 151 Milton Park, Abington, Oxon, OX 14 4SD, UK) in 1.7 mL THF was added by syringe pump over 1 h. The resulting mixture was stirred at −78° C. for 2 h, and then HMPA (2.2 mL, 12.6 mmol) was added followed by a solution of 19 (2.641 g, 8.7 mmol) in THF (1.6 mL). The reaction was stirred overnight at −40° C. and then was quenched by addition of 40 mL saturated ammonium chloride solution. A little water was added to dissolve the solids and the resulting mixture was extracted with ethyl acetate (3×30 mL). The combined ethyl acetate solution was dried (MgSO$_4$), filtered and evaporated. Purification by flash chromatography on silica gel (10% ethyl acetate/hexanes) gave the title ketone contaminated with ca. 35% of benzyl iodide 19 (438 mg).

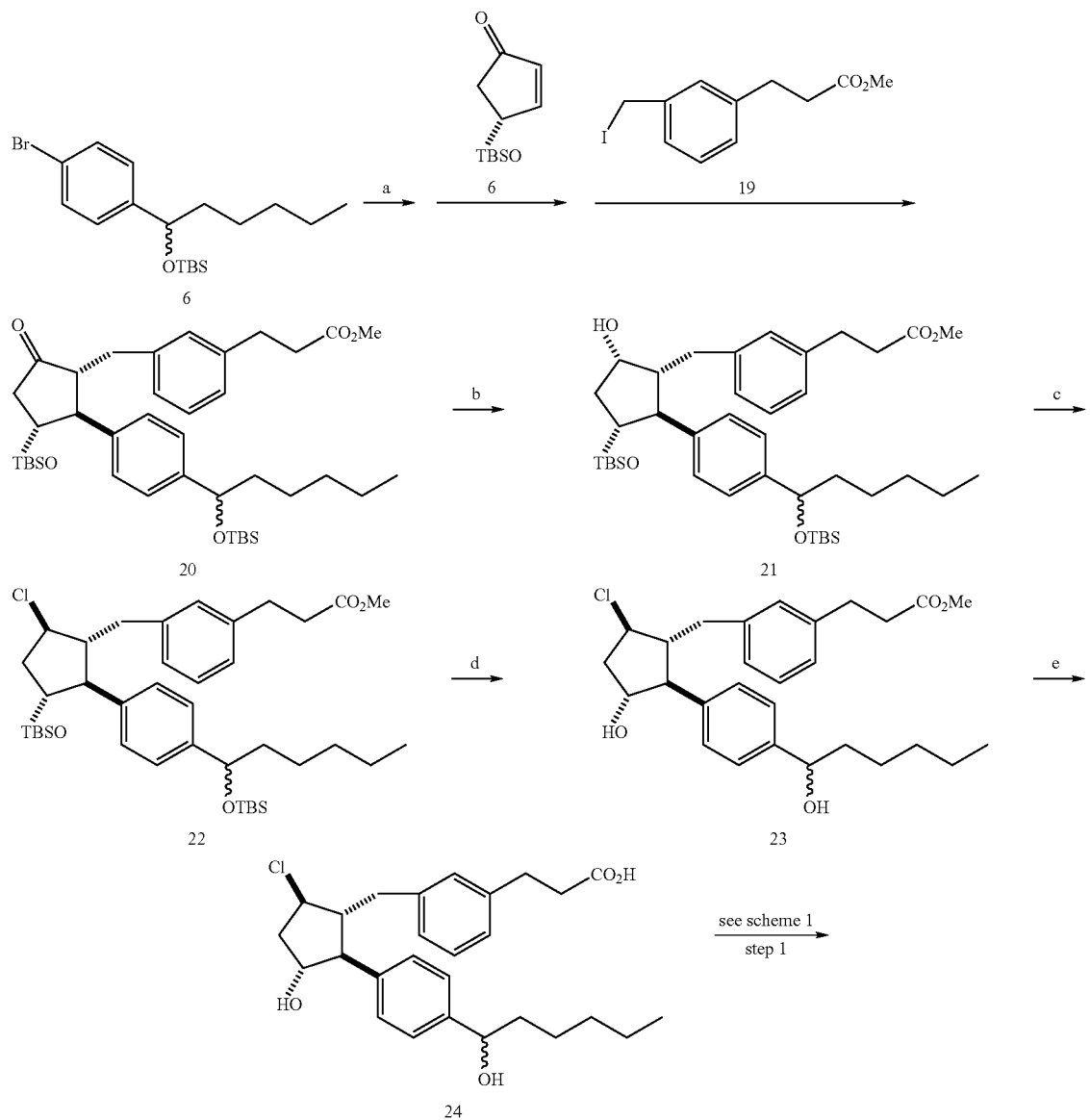

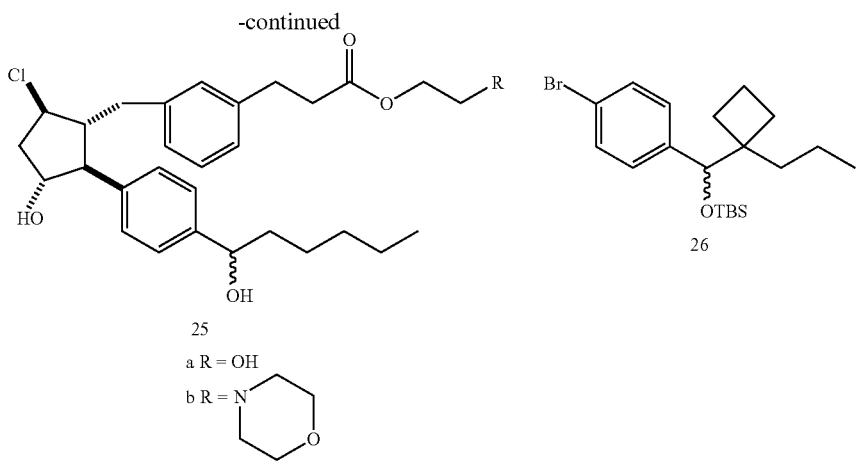

a R = OH
b R = N(morpholine)

(a) t-BuLi; Me₂Zn; (b) L-selectride; (c) MsCl, TEA; TBAC 40 °C.; (d) HF•pyridine; (e) aq. LiOH.

3-[3-((1R,2S,3R,5S)-3-(tert-Butyl-dimethyl-silanyloxy)-2-{4-[1-(tert-butyl-dimethyl-silanyloxy)-hexyl]-phenyl}-5-hydroxy-cyclopentylmethyl)-phenyl]-propionic acid methyl ester (21). The standard L-selectride procedure described in U.S. patent application Ser. No. 11/009,298, filed on Dec. 10, 2004 (now U.S. Pat. No. 7,091,231 issued Aug. 15, 2006) was used, which gave 224 mg (22% from enone 1-1) of pure compound 21.

3-2→→3-(3-{(1R,2S,3R,5R)-5-Chloro-3-hydroxy-2-[4-(1-hydroxy-hexyl)-phenyl]-cyclopentylmethyl}-phenyl)-propionic acid (24). The sequence was completed as shown in scheme 3 using the standard procedures described in U.S. patent application Ser. No. 11/009,298, filed on Dec. 10, 2004 (now U.S. Pat. No. 7,091,231 issued Aug. 15, 2006), FIG. 6.

3-[3-((1R,2S,3R,5R)-5-Chloro-3-hydroxy-2-{3-[hydroxy-(1-propyl-cyclobutyl)-methyl]-phenyl}-cyclopentylmethyl)-phenyl]-propionic acid methyl ester and 3-[3-((1R,2S,3R,5R)-5-Chloro-3-hydroxy-2-{3-[hydroxy-(1-propyl-cyclobutyl)-methyl]-phenyl}-cyclopentylmethyl)-phenyl]-propionic acid. The title compounds were prepared similarly to 23/24 starting with aryl bromide 3-6 (prepared as described in U.S. patent application Ser. No. 11/009,298, filed on Dec. 10, 2004 (now U.S. Pat. No. 7,091,231 issued Aug. 15, 2006) FIGS. 1,4).

Scheme 4

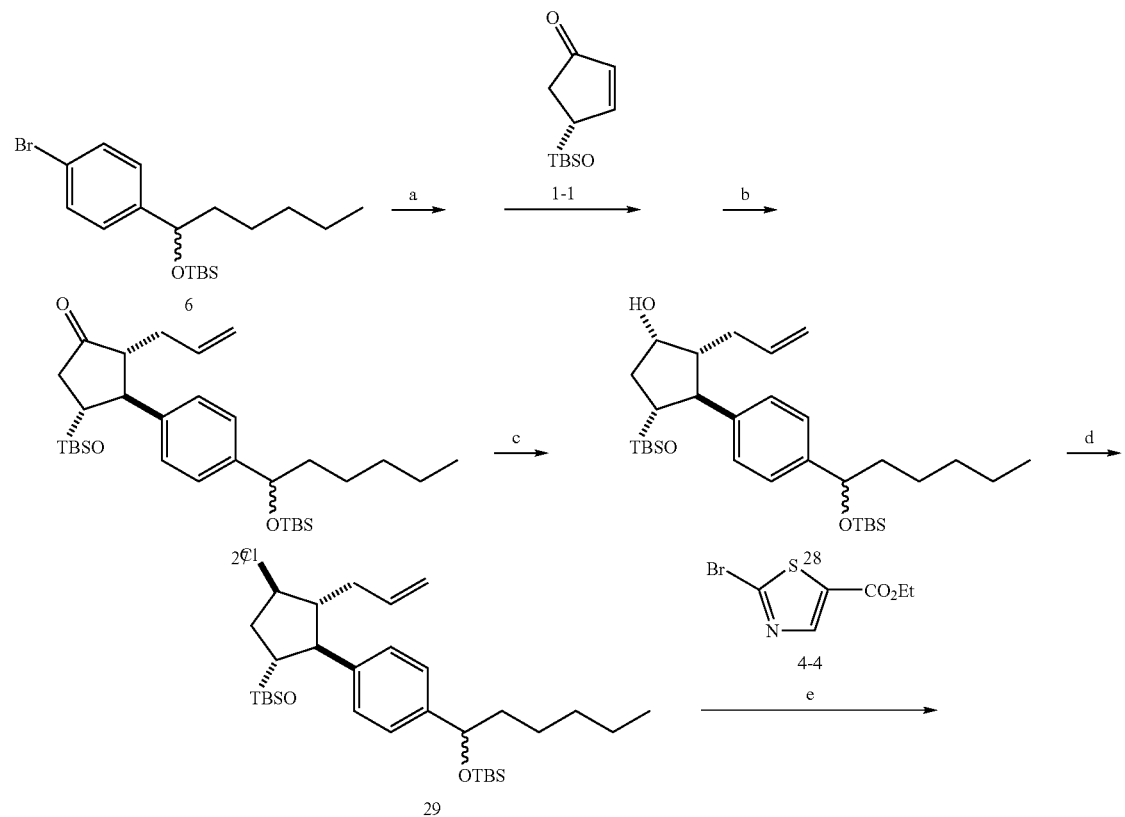

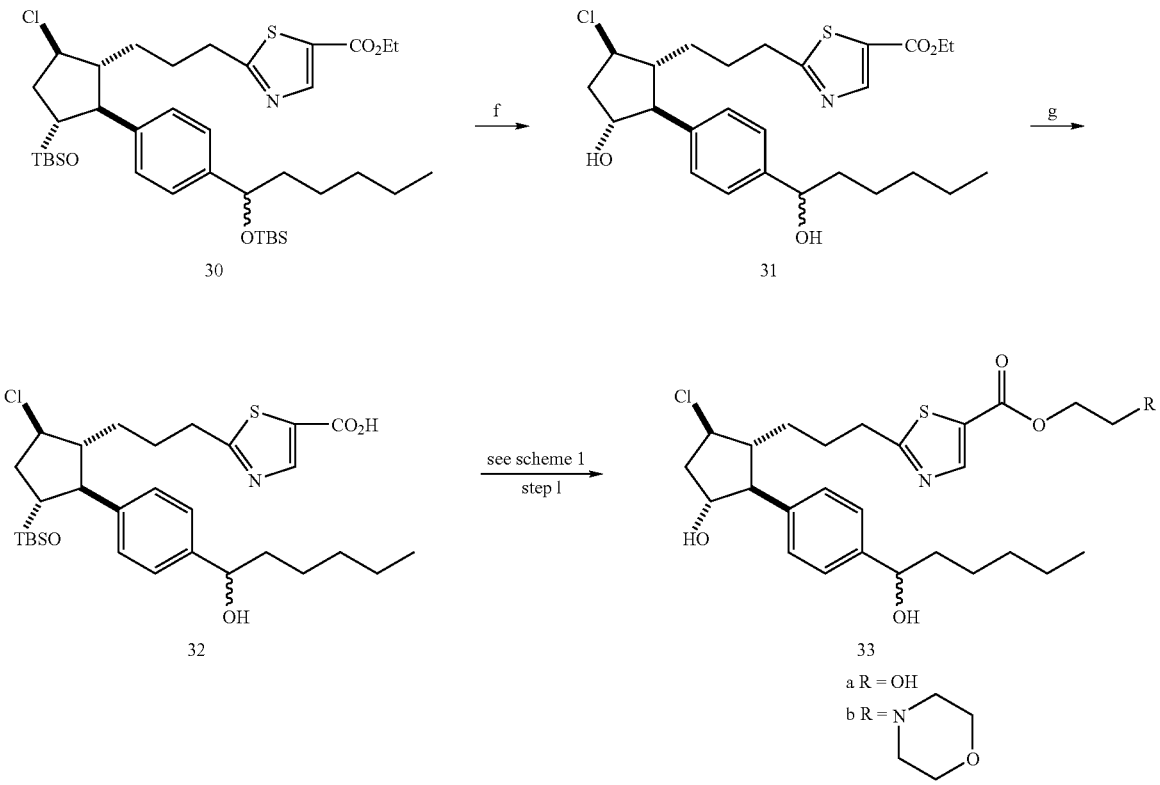

(a) t-BuLi; Me₂Zn; (b) allyl bromide, HMPA; (c) L-selectride; (d) MsCl, TEA; TBAC 40° C.;
(e) 9-BBN; PdCl₂(dppf), K₃PO₄, DMF 50° C.; (f) HF·pyridine 0° C.; (g) aq.LiOH, THF.

(2R,3S,4R)-2-Allyl-4-(tert-butyl-dimethyl-silanyloxy)-3-{4-[1-(tert-butyl-dimethyl-silanyloxy)-hexyl]-phenyl}-cyclopentanone (27). Compound 27 was prepared using an analogous procedure to that described for 20.

27→(1S,2R,3S,4R)-2-Allyl-4-tert-butyl-dimethyl-silanyloxy)-3-{4-[1-(tert-butyl-dimethyl-silanyloxy)-hexyl]-phenyl}-cyclopentanol (28)→1-[(1S,2R,3R,5R)-2-Allyl-5-(tert-butyl-dimethylsilanyloxy)-3-chloro-cyclopentyl]-4-[1-(tert-butyl-dimethyl-silanyloxy)-hexyl]-benzene (29). This sequence was performed as described in U.S. patent application Ser. No. 11/009,298, filed on Dec. 10, 2004 (now U.S. Pat. No. 7,091,231 issued Aug. 15, 2006), FIG. 6.

2-[3-(1R,2S,3R,5R)-3-(tert-Butyl-dimethyl-silanyloxy)-2-{4-[1-(tert-butyl-dimethyl-silanyloxy)-hexyl]-phenyl}-5-chloro-cyclopentyl)-propyl]-thiazole-5-carboxylic acid ethyl ester (31). A solution of 29 (39 mg, 0.069 mmol) in 0.2 mL THF was cannula transferred to a mixture of 9-BBN dimer (17 mg, 0.07 mmol) in 0.2 mL THF, rinsing with 0.2 mL THF. The reaction was placed in a 50° C. oil bath for 2.5 h, was allowed to cool to room temperature and H₂O (10 µL) was added. After 30 min., the solution was cannula transferred to a solution of ethyl 2-bromothiazole-5-carboxylate 4-4 (15 mg, 0.063 mmol) and PdCl₂(dppf) (5 mg, 0.007 mmol) in DMF (0.2 mL). K₃PO₄ (31 µL, 0.09 mmol, 3 M) was added and the solution was placed in a 50° C. oil bath. The reaction was stirred overnight and then partitioned between 15 mL ethyl acetate/15 mL water (a little brine was added). The aqueous layer was further extracted with 15 mL ethyl acetate and the combined ethyl acetate solution was dried (MgSO₄), filtered and evaporated. Purification by preparative TLC on silica gel (10% ethyl acetate/hexanes) gave compound 31 (4 mg, 0.0057 mmol, 8%).

31→2-(3-{(1R,2S,3R,5R)-5-Chloro-3-hydroxy-2-[4-(1-hydroxy-hexyl)-phenyl]-cyclopentyl}-propyl)-thiazole-5-carboxylic acid ethyl ester (32)→2-(3-{(1R,2S,3R,5R)-5-Chloro-3-hydroxy-2-[4-(1-hydroxy-hexyl)-phenyl]-cyclopentyl}-propyl)-thiazole-5-carboxylic acid (33). This sequence was performed as described in U.S. patent application Ser. No. 11/009,298, filed on Dec. 10, 2004 (now U.S. Pat. No. 7,091,231 issued Aug. 15, 2006), FIG. 6.

Conversion of 33 to 34a and 34b. This sequence is performed as described in scheme 1 step I.

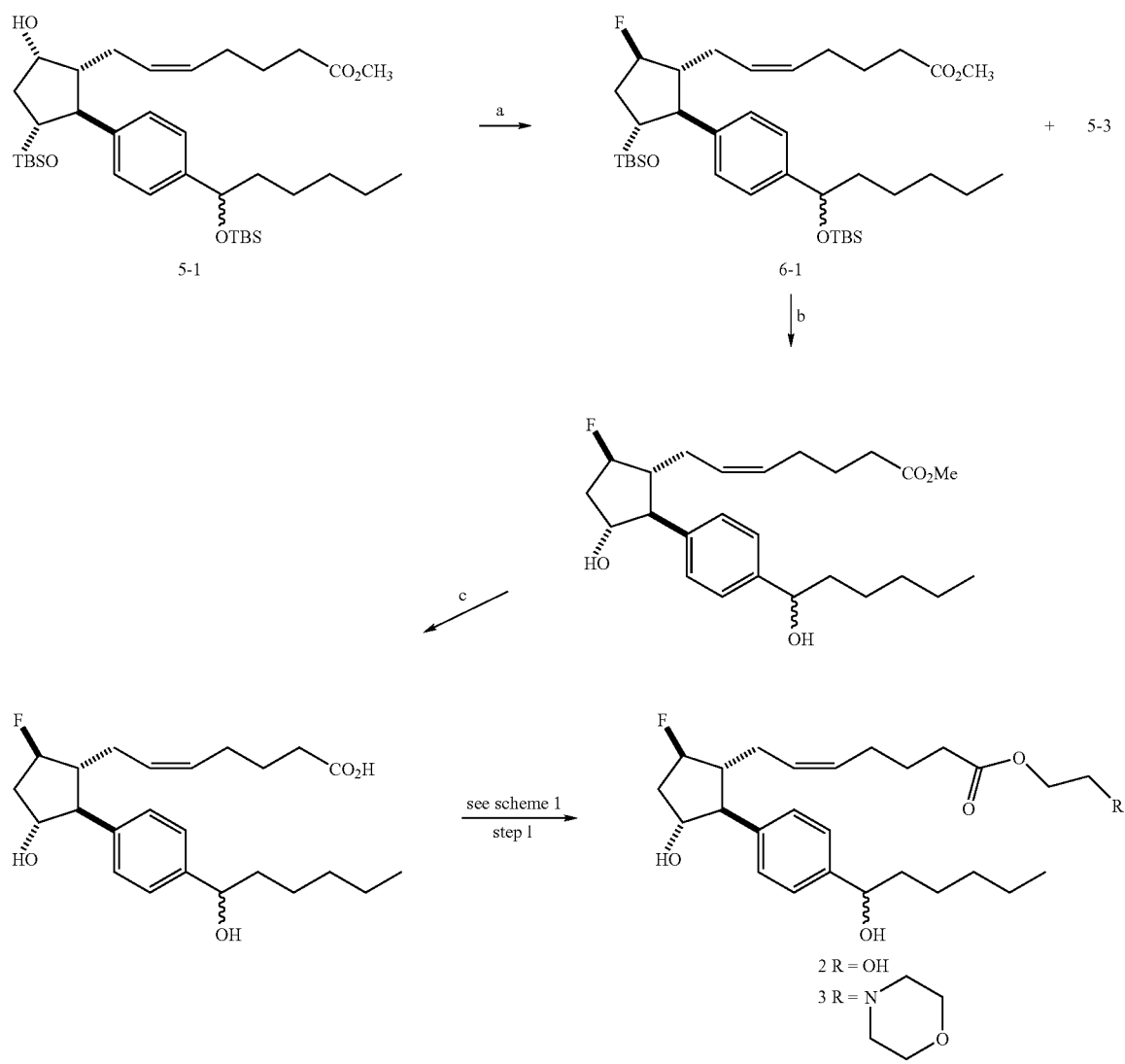

Scheme 6

(a) MsCl, TEA; NaCN, DMSO 80°; (b) HF·pyridine, 0° C.; (c) aq. LiOH, THF.

(Z)-7-((1R,2S,3R,5R)-3-(tert-Butyl-dimethyl-silanyloxy)-2-{4-[1-(tert-butyl-dimethyl-silanyloxy)-hexyl]-phenyl}-5-fluoro-cyclopentyl)-hept-5-enoic acid methyl ester (36). A solution of 35 (109 mg, 0.17 mmol) in 0.5 mL dichloromethane was cannula transferred to a −78° C. solution of deoxofluor [bis(2-methoxyethyl)aminosulfur trifluoride, 34 µL, 0.18 mmol) in 0.75 mL dichloromethane, rinsing with 0.25 mL dichloromethane. The reaction was stirred for 2 h at −78° C. and then was quenched by addition of 10 mL saturated NaHCO$_3$. The mixture was extracted with dichloromethane (3×15 mL) and the combined dichloromethane solution was dried (MgSO$_4$), filtered and evaporated. Purification by flash chromatography on silica gel (1% ethyl acetate/hexanes→2%) gave 25 mg (23%) of 37 and 53 mg of impure 36.

(Z)-7-{(1R,2S,3R,5R)-5-Fluoro-3-hydroxy-2-[4-(1-hydroxy-hexyl)-phenyl]-cyclopentyl}-hept-5-enoic acid methyl ester (38). The HF-pyridine procedure described in U.S. patent application Ser. No. 11/009,298, filed on Dec. 10, 2004 (now U.S. Pat. No. 7,091,231 issued Aug. 15, 2006) was followed, which gave 30 mg of impure 37 after flash chromatography on silica gel (40% ethyl acetate/hexanes). Further purification by preparative TLC (35% ethyl acetate/hexanes) gave 7 mg of pure 38.

(Z)-7-{(1R,2S,3R,5R)-5-Fluoro-3-hydroxy-2-[4-(1-hydroxy-hexyl)-phenyl]-cyclopentyl}-hept-5-enoic acid (39). The previously described LiOH procedure was used (U.S. patent application Ser. No. 11/009,298, filed on Dec. 10, 2004, now U.S. Pat. No. 7,091,231 issued Aug. 15, 2006).

Conversion of 39 to 40a and 40b. This sequence is performed as described in scheme 1 step I.

Scheme 7

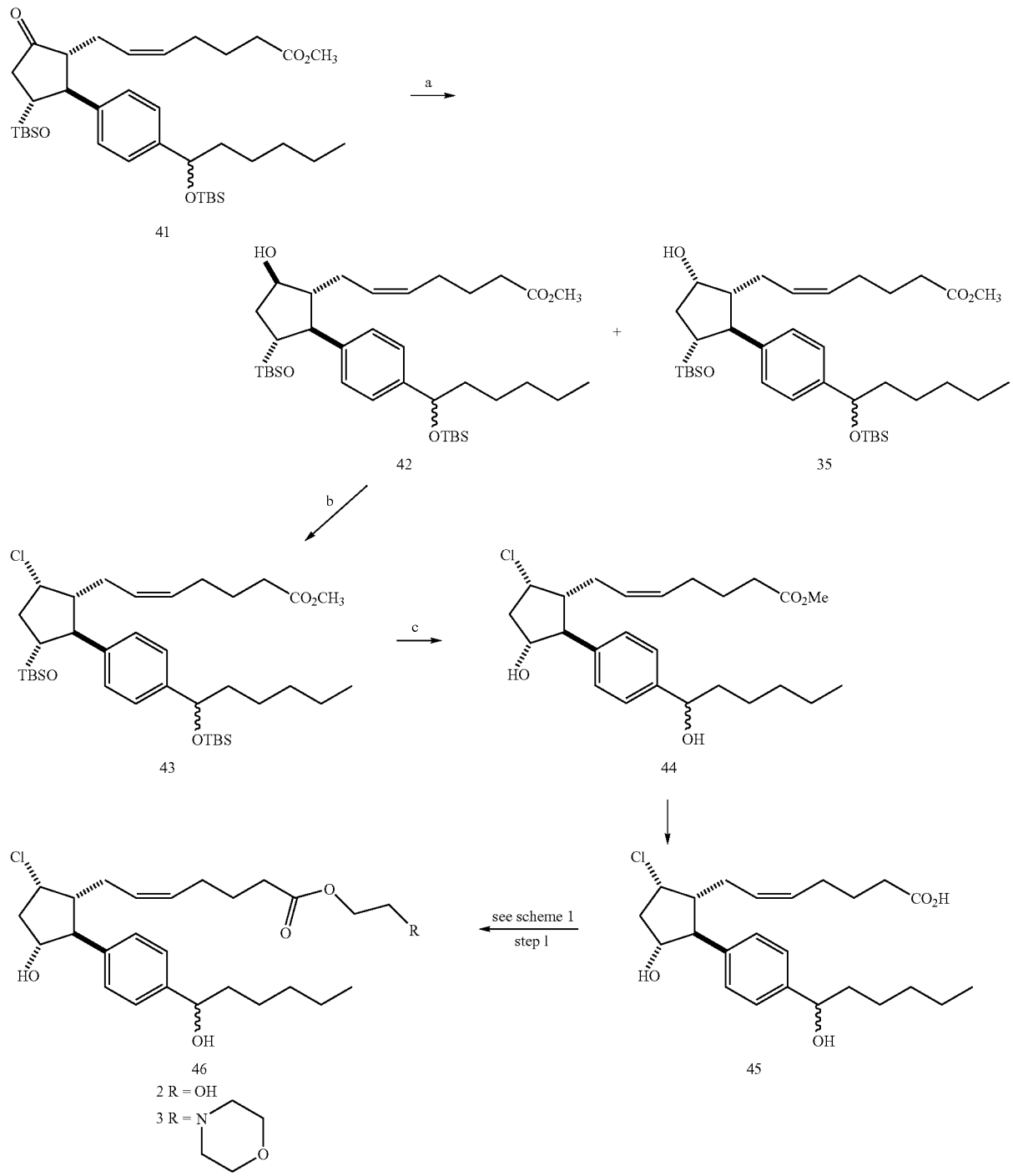

(a) NaBH₄; (b) MsCl, TEA; TBAC 80° C.; (c) HF•pyridine, 0° C.; (d) rabbit liver esterase.

(Z)-7-((1R,2S,3R,5S)-3-tert-Butyl-dimethyl-silanyloxy)-2-{4-[1-(tert-butyldimethyl-silanyloxy)-hexyl]-phenyl}-5-hydroxy-cyclopentyl)-hept-5-enoic acid methyl ester (35) and (Z)-7-((1R,2S,3R,5R)-3-(tert-Butyl-dimethyl-silanyloxy)-2-{4-[1-(tert-butyl-dimethyl-silanyloxy)-hexyl]-phenyl}-5-hydroxy-cyclopentyl)-hept-5-enoic acid methyl ester (42). NaBH₄ (9 mg, 0.24 mmol) was added to a solution of (Z)-7-((1R,2S,3R)-3-(tert-Butyl-dimethyl-silanyloxy)-2-{4-[1-(tert-butyl-dimethyl-silanyloxy)-hexyl]-phenyl}-5-oxo-cyclopentyl)-hept-5-enoic acid methyl ester (41) (55 mg, 0.087 mmol, prepared as described in U.S. patent application Ser. No. 11/009,298, filed on Dec. 10, 2004, (now U.S. Pat.

No. 7,091,231 issued Aug. 15, 2006, FIG. 5) in methanol (0.5 mL). After 20 min., 1 M HCl (10 mL) was added and the resulting mixture was extracted with dichloromethane (3×10 mL). The combined dichloromethane solution was dried (MgSO$_4$), filtered and evaporated. Purification by flash chromatography on silica gel (10% ethyl acetate/hexanes→15%) gave 27 mg (49%) of 42 and 16 mg (29%) of 35 along with an 8 mg mixed fraction.

(Z)-7-((1R,2S,3R,5S)-3-(tert-Butyl-dimethyl-silanyloxy)-2-{4-[1-(tert-butyl-dimethyl-silanyloxy)-hexyl]-phenyl}-5-chloro-cyclopentyl)-hept-5enoic acid methyl ester (43). Methanesulfonyl chloride (15 µL, 0.19 mmol) and triethylamine (30 µL, 0.21 mmol) were added to a solution of 42 (50 mg, 0.08 mmol) in dichloromethane (0.3 mL). After 1.5 h, saturated sodium bicarbonate solution (15 mL) was added and the resulting mixture was extracted with dichloromethane (3×15 mL). The combined dichloromethane solution was evaporated to give the crude mesylate.

The crude mesylate was taken into 0.7 mL toluene and (n-Bu)$_4$NCl (246 mg, 0.90 mmol) was added. The mixture was stirred at 80° C. for 1 h and then was filtered through silica gel (20% ethyl acetate/hexanes) to give 43 (40 mg, 77%).

43→(Z)-7-{(1R,2S,3R,5S)-5-Chloro-3-hydroxy-2-[4-(1-hydroxy-hexyl)-phenyl]-cyclopentyl}-hept-5-enoic acid methyl ester (44) 44→(Z)-7-{(1R,2S,3R,5S)-5-Chloro-3-hydroxy-2-[4-(1-hydroxy-hexyl)-phenyl]-cyclopentyl}-hept-5-enoic acid (45). This sequence was completed as shown in scheme 7, following procedures described in U.S. patent application Ser. No. 11/009,298, filed on Dec. 10, 2004 (now U.S. Pat. No. 7,091,231 issued Aug. 15, 2006).

Conversion of 45 to 46a and 46b. This sequence is performed as described in scheme 1 step I.

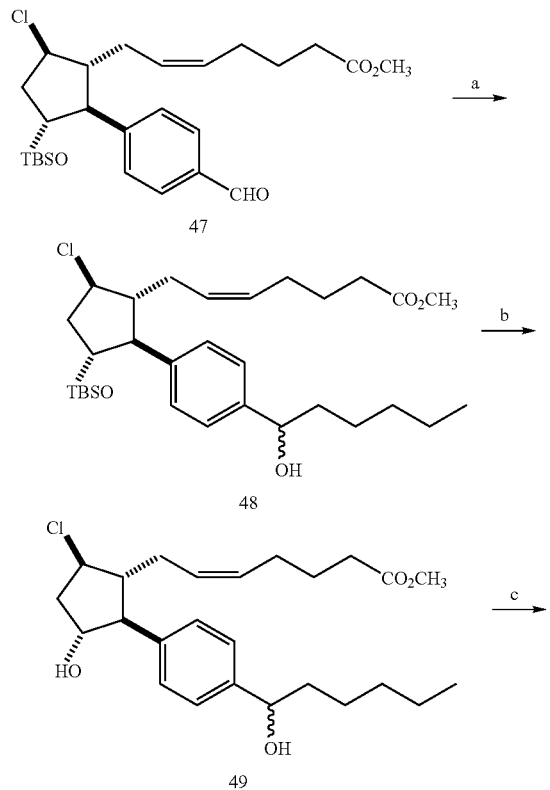

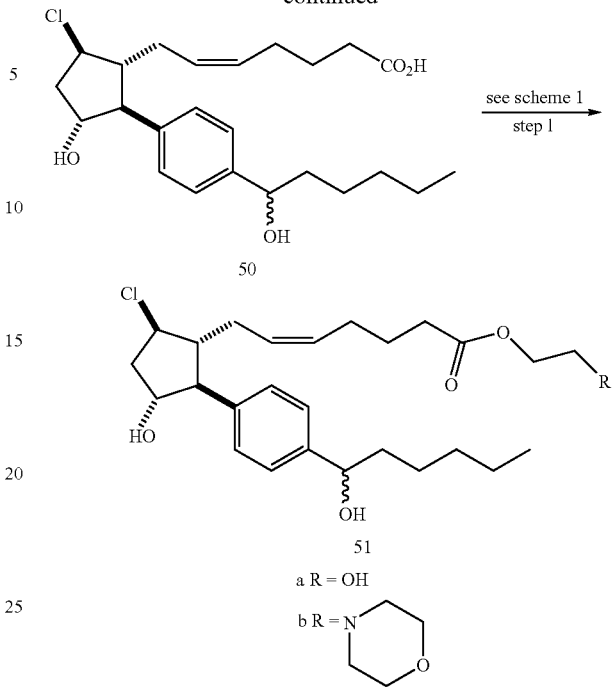

(a) n-pentylMgBr; (b) HF-pyridine 0° C.;
(c) 1 M LiOH, THF; (d) 2-iodopropane, DBU, acetone.

(Z)-7-{(1R,2S,3R,5R)-5-Chloro-3-hydroxy-2-[4-(1-hydroxy-hexyl)-phenyl]-cyclopentyl}-hept-5-enoic acid (50). The title compound was prepared as shown in scheme 8, in a similar manner to that described in U.S. patent application Ser. No. 11/009,298, filed on Dec. 10, 2004, (now U.S. Pat. No. 7,091,231 issued Aug. 15, 2006), FIG. 9.

(Z)-7-{(1R,2S,3R,5R)-5-Chloro-3-hydroxy-2-[4-(1-hydroxy-hexyl)-phenyl]-cyclopentyl}-hept-5-enoic acid isopropyl ester (51). This compound was prepared using the standard procedure described in U.S. patent application Ser. No. 11/009,298, filed on Dec. 10, 2004 (now U.S. Pat. No. 7,091,231 issued Aug. 15, 2006).

Preparation of the individual diastereomers of 50. The individual diastereomers were separated by preparative HPLC at the stage of 48: ca. 5 mg sample/run; Chiralcel OD semiprep column (1×25 cm), 2.4 mL/min. flow rate, 10% isopropyl alcohol/hexanes; retention times=17.6 min. and 23.8 min. The individual diastereomers were then taken on separately as shown in scheme 8 and as described in U.S. patent application Ser. No. 11/009,298, filed on Dec. 10, 2004 (now U.S. Pat. No. 7,091,231 issued Aug. 15, 2006).

Conversion of 50 to 51a and 51b. This sequence is performed as described in scheme 1 step I.

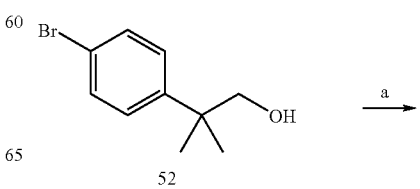

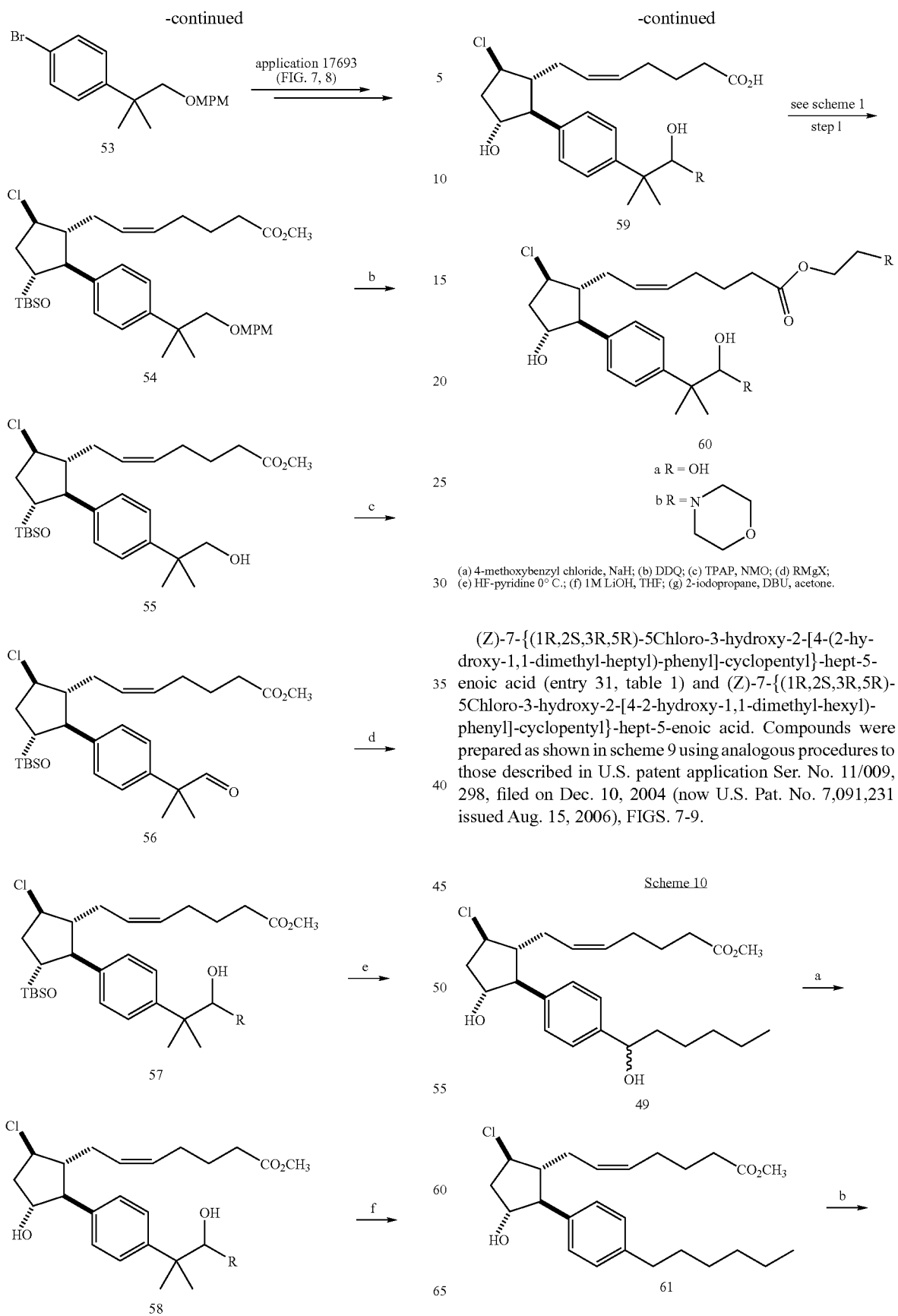

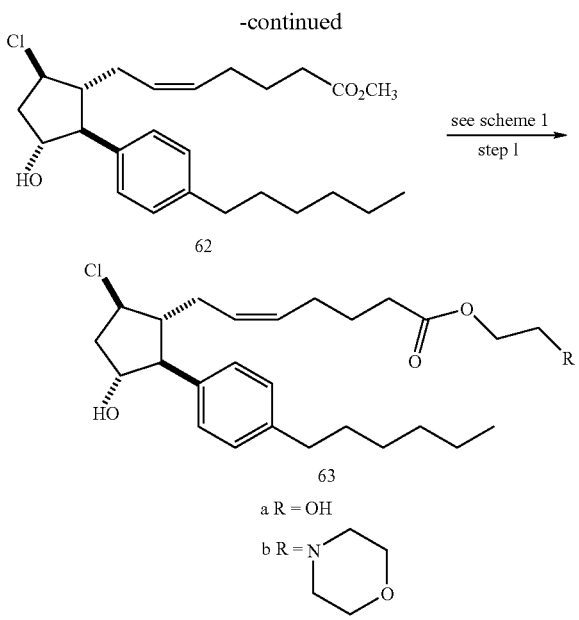

(a) Et₃SiH, TFA, ClCH₂CH₂Cl; (b) aq. LiOH, THF.

(Z)-7-[(1R,2S,3R,5R)-5-Chloro-2-(4-hexyl-phenyl)-3-hydroxy-cyclopentyl]-hept-5-enoic acid methyl ester (61). Et₃SiH (30 □L, 0.19 mmol) followed by TFA (90 □L, 1.17 mmol) were added to a solution of 49 (23 mg, 0.046 mmol) in dichloroethane (0.10 mL). After 15 min., the reaction was quenched by addition of 4 mL saturated sodium bicarbonate solution. The resulting mixture was extracted with dichloromethane (3×30 mL) and the combined dichloromethane solution was dried (Na₂SO₄), filtered and evaporated. Purification by flash chromatography on silica gel (10% ethyl acetate/hexanes→15%→20%) gave 21 mg (110%) of 61.

(Z)-7-[(1R,2S,3R,5R)-5-Chloro-2-(4-hexyl-phenyl)-3-hydroxy-cyclopentyl]-hept-5-enoic acid (62). The title compound was prepared using the standard LiOH procedure described in U.S. patent application Ser. No. 11/009,298, filed on Dec. 10, 2004 (now U.S. Pat. No. 7,091,231 issued Aug. 15, 2006).

Conversion of 62 to 63a and 63b. This sequence is performed as described in scheme 1 step I.

Scheme 11

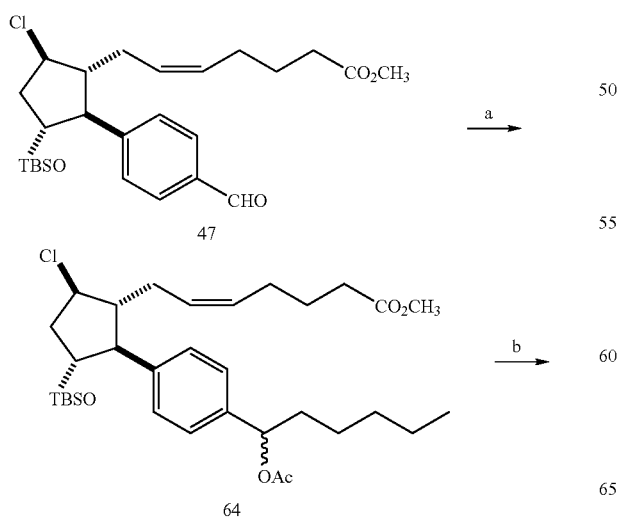

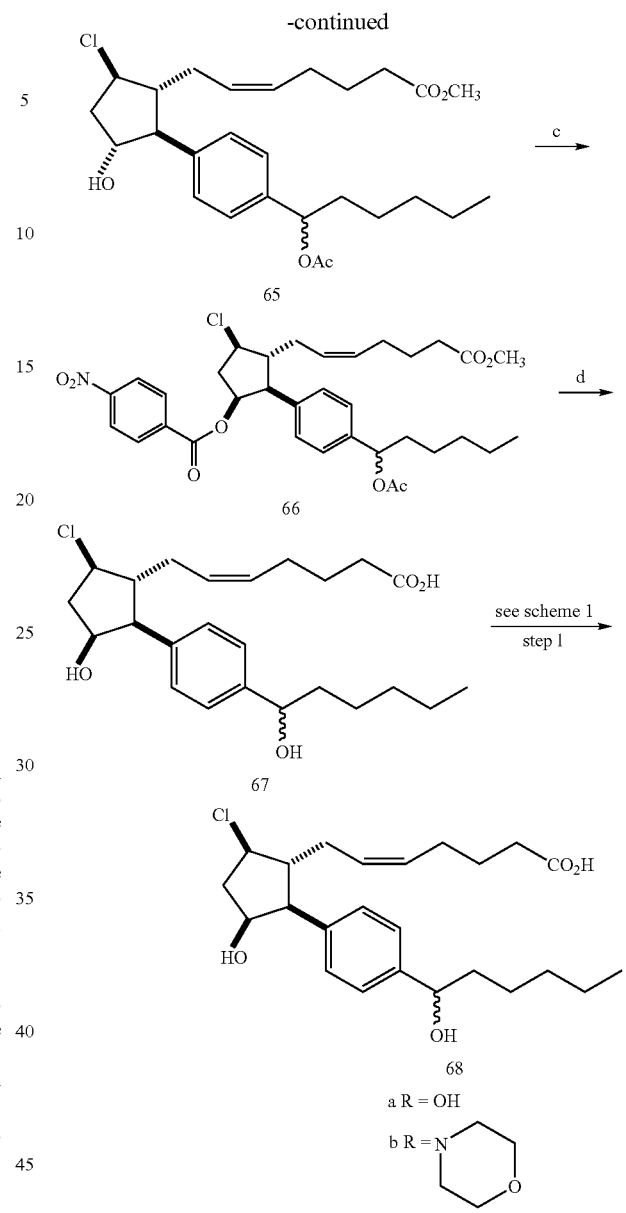

(a) n-pentylMgBr; EtOAc; (b) HF-pyridine 0° C.;
(c) Ph₃P, diisopropyl azodicarboxylate, 4-nitrobenzoic acid, THF;
(d) 1M LiOH, THF.

(Z)-7-[(1R,2S,3R,5R)-2-[4-(1-Acetoxy-hexyl)-phenyl]-3-(tert-butyl-dimethyl-silanyloxy)-5-chloro-cyclopentyl]-hept-5-enoic acid methyl ester (64). n-PentylMgBr (130 □L, 0.26 mmol) was added to a 0° C. solution of 47 (114 mg, 0.24 mmol) in THF (0.9 mL). After 2.5 h, 1 mL ethyl acetate was added and the reaction was allowed to warm to room temperature. After 30 min. at room temperature, 10 mL saturated ammonium chloride solution was added and the resulting mixture was extracted with ethyl acetate (3×30 mL). The combined ethyl acetate solution was dried (Na₂SO₄), filtered and evaporated. Purification by flash chromatography on silica gel (10% ethyl acetate/hexanes) gave 113 mg (80%) of 64.

(Z)-7-{(1R,2S,3R,5R)-2-[4-(1-Acetoxy-hexyl)-phenyl]-5-chloro-3-hydroxy-cyclopentyl}-hept-5-enoic acid methyl ester (65). The standard HF.pyridine deprotection described in U.S. patent application Ser. No. 11/009,298, filed on Dec. 10, 2004 (now U.S. Pat. No. 7,091,231 issued Aug. 15, 2006) was used.

4-Nitro-benzoic acid (1S,2S,3R,4R)-2-[4-(1-acetoxy-hexyl)-phenyl]-4-chloro-3-((Z)-6-methoxycarbonyl-hex-2-enyl)-cyclopentyl ester (66). Diisopropyl azodicarboxylate (11 □L, 0.057 mmol) was added to a mixture of $Ph_3P$ (15.6 mg, 0.059 mmol), 4-nitrobenzoic acid (8.3 mg, 0.050 mmol), and 65 (17 mg, 0.036 mmol) in THF (0.600 mL). The reaction was stirred overnight and then the volatiles were evaporated in vacuo. Purification of the residue by flash chromatography on silica gel (30% ethyl acetate/hexanes) gave 10 mg (45%) of 66.

(Z)-7-{(1R,2S,3S,5R)-5-Chloro-3-hydroxy-2-[4-(1-hydroxy-hexyl)-phenyl]cyclopentyl}-hept-5-enoic acid (67). The standard LiOH hydrolysis procedure described in U.S. patent application Ser. No. 11/009,298, filed on Dec. 10, 2004 (now U.S. Pat. No. 7,091,231 issued Aug. 15, 2006) was used.

Conversion of 67 to 68a and 68b. This sequence is performed as described in scheme 1 step I.

In Vivo Examples

Compounds from above are tested in vivo to measure its ability to reduce intraocular pressure. Compound 14a is tested in normotensive dogs. The intraocular pressure (IOP) decreases from baseline. This compound is also tested in laser-induced hypertensive monkeys, the IOP decreases from baseline.

Compound 14b is tested in normotensive dogs. The intraocular pressure (IOP) decreases from baseline. This compound is also tested in laser-induced hypertensive monkeys, the IOP decreases from baseline.

Compound 25a is tested in normotensive dogs. The intraocular pressure (IOP) decreases from baseline. This compound is also tested in laser-induced hypertensive monkeys, the IOP decreases from baseline.

Compound 25b is tested in normotensive dogs. The intraocular pressure (IOP) decreases from baseline. This compound is also tested in laser-induced hypertensive monkeys, the IOP decreases from baseline.

Compound 34a is tested in normotensive dogs. The intraocular pressure (IOP) decreases from baseline. This compound is also tested in laser-induced hypertensive monkeys, the IOP decreases from baseline.

Compound 34b is tested in normotensive dogs. The intraocular pressure (IOP) decreases from baseline. This compound is also tested in laser-induced hypertensive monkeys, the IOP decreases from baseline.

Compound 40a is tested in normotensive dogs. The intraocular pressure (IOP) decreases from baseline. This compound is also tested in laser-induced hypertensive monkeys, the IOP decreases from baseline.

Compound 40b is tested in normotensive dogs. The intraocular pressure (IOP) decreases from baseline. This compound is also tested in laser-induced hypertensive monkeys, the IOP decreases from baseline.

Compound 46a is tested in normotensive dogs. The intraocular pressure (IOP) decreases from baseline. This compound is also tested in laser-induced hypertensive monkeys, the IOP decreases from baseline.

Compound 46b is tested in normotensive dogs. The intraocular pressure (IOP) decreases from baseline. This compound is also tested in laser-induced hypertensive monkeys, the IOP decreases from baseline.

Compound 51a is tested in normotensive dogs. The intraocular pressure (IOP) decreases from baseline. This compound is also tested in laser-induced hypertensive monkeys, the IOP decreases from baseline.

Compound 51b is tested in normotensive dogs. The intraocular pressure (IOP) decreases from baseline. This compound is also tested in laser-induced hypertensive monkeys, the IOP decreases from baseline.

Compound 60a is tested in normotensive dogs. The intraocular pressure (IOP) decreases from baseline. This compound is also tested in laser-induced hypertensive monkeys, the IOP decreases from baseline.

Compound 60b is tested in normotensive dogs. The intraocular pressure (IOP) decreases from baseline. This compound is also tested in laser-induced hypertensive monkeys, the IOP decreases from baseline.

Compound 63a is tested in normotensive dogs. The intraocular pressure (IOP) decreases from baseline. This compound is also tested in laser-induced hypertensive monkeys, the IOP decreases from baseline.

Compound 63b is tested in normotensive dogs. The intraocular pressure (IOP) decreases from baseline. This compound is also tested in laser-induced hypertensive monkeys, the IOP decreases from baseline.

Compound 68a is tested in normotensive dogs. The intraocular pressure (IOP) decreases from baseline. This compound is also tested in laser-induced hypertensive monkeys, the IOP decreases from baseline.

Compound 68b is tested in normotensive dogs. The intraocular pressure (IOP) decreases from baseline. This compound is also tested in laser-induced hypertensive monkeys, the IOP decreases from baseline.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, commercially provides pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

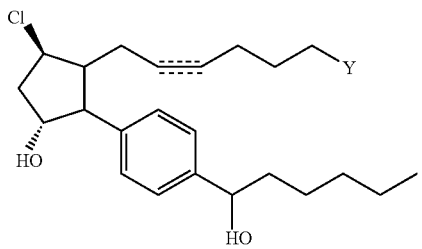

wherein Y is

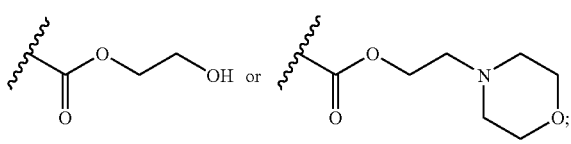

or a pharmaceutically acceptable salt thereof, wherein a dashed line indicates the presence or absence of a bond.

2. The compound of claim 1 of the formula

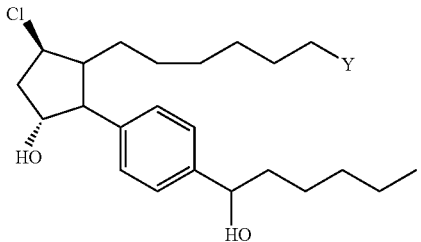

or a pharmaceutically acceptable salt thereof.

3. The compound of claim 1 of the formula

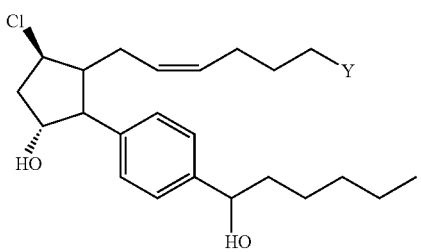

or a pharmaceutically acceptable salt thereof.

4. The compound of claim 3 of the formula

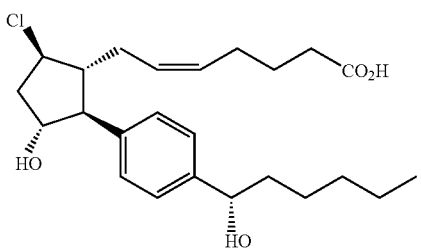

or a pharmaceutically acceptable salt thereof.

5. The compound of claim 1 of the formula

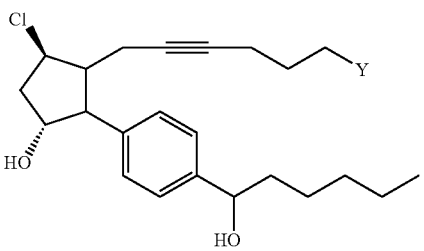

or a pharmaceutically acceptable salt thereof.

6. A method of treating baldness comprising administering a compound of claim 1 to a mammal in need thereof.

* * * * *